(12) United States Patent
Mehanna et al.

(10) Patent No.: US 6,951,860 B2
(45) Date of Patent: Oct. 4, 2005

(54) CALCIUM CHANNEL BLOCKERS

(75) Inventors: Ahmed S. Mehanna, Sudbury, MA (US); Jinyung T. Kim, Boston, MA (US)

(73) Assignee: Massachusetts College of Pharmacy, Boston, MA (US)

( * ) Notice: Subject to any disclaimer, the term of this patent is extended or adjusted under 35 U.S.C. 154(b) by 183 days.

(21) Appl. No.: 09/998,623

(22) Filed: Oct. 31, 2001

(65) Prior Publication Data

US 2002/0115655 A1 Aug. 22, 2002

Related U.S. Application Data

(62) Division of application No. 08/982,953, filed on Dec. 2, 1997, now Pat. No. 6,541,479.

(51) Int. Cl.$^7$ .......................................... A61K 31/4965
(52) U.S. Cl. ............................. 514/252.12; 514/252.13; 514/255.03; 514/255.04; 514/613; 514/617; 514/618; 514/310; 514/255.4
(58) Field of Search ........................ 514/252.12, 252.13, 514/255.03, 255.04, 613, 617, 618, 619

(56) References Cited

U.S. PATENT DOCUMENTS

| | | | |
|---|---|---|---|
| 4,550,116 A | 10/1985 | Soto et al. ................... 514/327 |
| 4,593,033 A | 6/1986 | Hartman et al. ............. 514/290 |
| 4,596,805 A | 6/1986 | Jiang ....................... 514/264.1 |
| 4,640,930 A | 2/1987 | Mohacsi et al. ............. 514/431 |
| 4,654,353 A | 3/1987 | Alker et al. ................. 514/334 |
| 4,742,069 A | 5/1988 | Jaunin et al. ............... 514/356 |
| 4,758,669 A | 7/1988 | Johnson et al. ............. 541/263 |
| 4,791,117 A | 12/1988 | Press ......................... 514/300 |
| 4,829,076 A | 5/1989 | Szilagyi et al. ............. 514/356 |
| 4,847,273 A | 7/1989 | Jaunin et al. ............... 514/347 |
| 4,918,073 A | 4/1990 | Riiger et al. ............. 514/252.12 |
| 4,918,074 A | 4/1990 | Tsuda et al. ............ 514/252.12 |
| 4,959,359 A | 9/1990 | Mohacsi et al. ........ 514/211.03 |
| 4,988,713 A | 1/1991 | Frigerio et al. ............. 514/356 |
| 4,992,432 A | 2/1991 | Mohacsi et al. ........ 514/211.03 |
| 4,994,612 A | 2/1991 | Jaunin et al. ................. 564/88 |
| 5,017,586 A | 5/1991 | Schlager ..................... 514/318 |
| 5,025,010 A | 6/1991 | Oekonomopulos et al. ........................ 514/224.2 |
| 5,034,395 A | 7/1991 | Tamada et al. ............. 514/277 |
| 5,036,098 A | 7/1991 | Kimura et al. ............. 514/438 |
| 5,039,674 A | 8/1991 | Fujikura et al. ........ 514/217.04 |
| 5,070,088 A | 12/1991 | Atwal ..................... 514/212.08 |
| 5,071,844 A | 12/1991 | Alker et al. ............. 514/211.11 |
| 5,106,845 A | 4/1992 | Carr et al. ................... 514/218 |
| 5,132,106 A | 7/1992 | Tuloup et al. ............. 514/223.5 |
| 5,134,139 A | 7/1992 | Kawai et al. ............ 514/211.07 |
| 5,135,936 A | 8/1992 | Adams et al. .............. 514/305 |
| 5,144,029 A | 9/1992 | Ward et al. ................. 540/610 |
| 5,198,433 A | 3/1993 | Palfreyman et al. ... 514/217.11 |
| 5,276,026 A | 1/1994 | Barrish et al. ......... 514/212.02 |
| 5,281,592 A | 1/1994 | Ozeki et al. ............. 514/224.2 |
| 5,344,830 A | 9/1994 | Mills et al. ............... 514/235.8 |
| 5,360,809 A | 11/1994 | Axelsson et al. ........... 514/338 |
| 5,387,592 A | 2/1995 | Bradbury et al. ........... 514/312 |
| 5,496,815 A | 3/1996 | Ozeki et al. ............. 514/224.2 |
| 5,514,693 A | 5/1996 | Cozzi et al. ................ 514/341 |
| 5,607,939 A | 3/1997 | Kato et al. ................. 514/278 |
| 5,623,051 A | 4/1997 | Catterall et al. ............ 530/324 |

OTHER PUBLICATIONS

Gialdi et al., Abstract to CA 56:4664g.*
McMurry, John, Editor of Second Edition, Organic Chemistry, 1984, pp. 742–746.*
Protiva, et al. of CZ 105,590 of CA59:10010f, Nov. 15, 1962.*
Goodman & Gilman's The Pharmacological Basis of Therapeutics, 9th Edition, pp. 767–774, 1996.*
Gialdi, et al., Chemical Abstracts, Mar. 8, 1962, 4664g, vol. 56, No. 5, The American Chemical Society.
Fujita, M. et al, "Synthesis and Ca$^{2+}$ Antagonistic Activity of 2-[2-[(Aminoalkyl)oxy]-5-methoxyphenyl]-3, 4-dihydro-4-methyl-3-oxo-2H-1,4-benzo-thiazines", J. Med. Chem., 1990, pp. 1898–1905, vol. 33, American Chemical Society.
Yamamoto, K, et al., "Novel Calcium Antagonists. Synthesis and Structure–Activity Relationship Studies of Benzothiazoline Derivatives", J. Med. Chem., 1988, pp. 919–930, vol. 31, American Chemical Society.
Jilek, J.; et al., "Preparation of new antimicrobial (phenylthio)benzylamines", Chemical Abstracts Accession No. 1992:612134 (Abstract only).
Jilek, J., et al., "Potential antidepressasnts: 2-(methyoxy- and hydroxyphenylthio)benzylamines as selective inhibitors of 5-hydroxytryptamine re-uptake in the brain", Chemical Abstracts Accession No. 1990:458496 (Abstract only).

* cited by examiner

Primary Examiner—Dwayne Jones
(74) Attorney, Agent, or Firm—Wolf, Greenfield & Sacks, PC

(57) ABSTRACT

The invention involves the identification of a family of compounds which block calcium channels. The compounds can be formulated in pharmaceutical carriers and administered to subjects. The compounds are useful for treating disorders associated with calcium channel activity, such as, cardiovascular diseases, for example hypertension, congestive heart failure, arrhythmia and angina.

4 Claims, 4 Drawing Sheets

CALCIUM CHANNEL BLOCKERS

RELATED APPLICATIONS

This application is a divisional of Ser. No. 08/982,953, filed on Dec. 2, 1997, which is now U.S. Pat. No. 6,541,479.

FIELD OF THE INVENTION

This invention relates to a class of aromatic compounds which are blockers of calcium channels. The invention also relates to pharmaceutical compositions, methods of blocking calcium channels, kits and methods of treatment using the class of compounds described herein, as well as intermediate compounds useful in the preparation of the compounds.

BACKGROUND OF THE INVENTION

Calcium channel blockers are a chemically diverse class of compounds having important therapeutic value in the control of a variety of diseases including several cardiovascular disorders, such as hypertension, angina, and cardiac arrhythmias (Fleckenstein, *Cir. Res.* v. 52, (suppl. 1), p.13–16 (1983); Fleckenstein, *Experimental Facts and Therapeutic Prospects,* John Wiley, New York (1983); McCall, D., *Curr Pract Cardiol,* v. 10, p. 1–11 (1985)).

Calcium channel blockers are a heterogenous group of drugs that prevent or slow the entry of calcium into cells by regulating cellular calcium channels. (Remington, *The Science and Practice of Pharmacy,* Nineteenth Edition, Mack Publishing Company, Eaton, Pa., p.963 (1995)). The regulation of calcium entry into the cells of the cardiovascular system is of paramount importance to the proper functioning of this system. Cardiac and vascular smooth muscle cells have calcium channels within the cell membrane. Calcium influx through these channels initiates a process of electro-mechanical coupling which ultimately leads to muscle contraction. The ability to regulate the entry of calcium into cardiac and vascular smooth muscle cells is a powerful therapeutic approach in the treatment of angina and hypertension respectively. Likewise, blocking calcium influx into cardiac tissues and conduction systems provides a useful approach to control certain types of arrhythmia.

Calcium channel blockers are also believed to be useful in the treatment of other disorders in which the regulation of calcium plays a role in normal hemostasis. Such disorders include, for example, pulmonary hypertension, peripheral vascular disease, mild congestive heart failure, hypertrophic subaortic stenosis, protection against ischemic injury, stroke, migraine, tumor resistance to anti-neoplastic drugs, achalasia, esophageal spasms, bronchial asthma, premature labor, dysmenorrhea, and enhancement of success in renal transplantation. (Remington, *The Science and Practice of Pharmacy,* Nineteenth Edition, Mack Publishing Company, Eaton, Pa., p.963 (1995)).

Most of the currently available calcium channel blockers belong to one of three major chemical groups of drugs, the dihydropyridines, such as nifedipine, the phenyl alkyl amines, such as verapamil, and the benzothiazepines such as diltiazem. While the structure activity relationships (SAR) of the dihydropyridines and the phenyl alkyl amines are well defined and extensively studied, very limited information is available on the SAR of benzothiazepines such as diltiazem. Diltiazem is a chiral molecule, with a seven membered fused-ring system, having a thiazepine, which is fused with a benzene ring. The structure is further characterized by three key functional groups, a 4-methoxybenzyl substituent at position "2"; an actoxy ester at position "3"; and positions "4" and "5" forming an amide function with N,N-dimethylaminoethyl substitution at the amide nitrogen. Scientists at central research laboratory at Osaka, Japan, synthesized a series of potent calcium channel blockers in which the seven membered ring of diltiazem was replaced with 6- and 5- membered fused-ring systems. These two new classes of calcium channel blockers, the benzothiazine and benzothiazole respectively (Yamamoto, K., *J. Med. Chem.,* v.31, p. 919–930 (1988); Fujita, M., *J. Med. Chem., v.* 33, p. 1898–1905 (1990)) demonstrated potent calcium channel blocking activity. Some of these compounds even demonstrated more tissue selectivity toward calcium channels in blood vessels.

SUMMARY OF THE INVENTION

A new family of calcium channel blockers, which are defined by the structures set forth below, have been identified according to the invention. The members of the new family of compounds constitute a new class of calcium channel blockers which is not encompassed by any of the three known classes of calcium channel blockers, the dihydropyridines, the phenyl alkyl amines, or the benzothiazepines. Of the three known classes the compounds of the invention are most structurally similar to the benzothiazepine class of calcium channel blockers, which have the following structural formula.

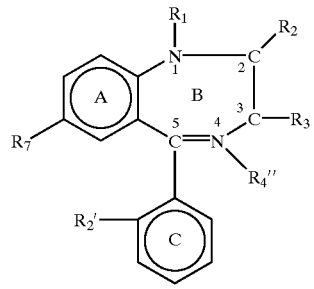

Prior to the instant invention it was believed that the fused ring structure of the benzothiazepines was essential for the calcium channel blocking activity of these compounds. Applicants, however, have surprisingly discovered that compounds having the basic central atomic structure of the benzothiazepines but lacking the fused ring structure have calcium channel blocking activity and actually demonstrate comparable anti-hypertensive activity to traditional benzothiazepines such as diltiazem.

In one aspect the invention is a composition of a compound having the following structural formula:

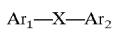

wherein $Ar_2$ is an aryl group or a heteroaryl group, wherein the heteroaryl is a ring having 5, 6, or 7 atoms, and wherein at least one atom of the heteroaryl is selected from the group consisting of a sulfur, a nitrogen, and an oxygen atom, and which is substituted with $R_1$, $R_2$, $R_3$, $R_4$, and $R_5$;

wherein $Ar_1$ is an aryl group or a heteroaryl group, wherein the heteroaryl is a ring having 5, 6, or 7 atoms, and wherein at least one atom of the heteroaryl is selected from the group consisting of a sulfur, a nitrogen, and an oxygen atom, and which is substituted with $R_6$, $R_7$, $R_8$, $R_9$, and $R_{10}$;

wherein $R_1$, $R_2$, $R_3$, $R_4$, $R_5$, $R_7$, $R_8$, $R_9$, and $R_{10}$ independent of one another, are selected from the group consisting of —H, halogen, piperonyl, ($C_1$–$C_6$) alkyl, ($C_1$–$C_6$) alkenyl, ($C_1$–$C_6$) alkynyl, ($C_1$–$C_6$) alkoxy —CN, —OR', —SR', —NO$_2$, —NR'R', amino acid, —C(O)R', —C(S)R', —C(O)OR', —C(S)OR', —C(O)SR', —C(S)SR', —C(O)N(R')$_2$, —C(O)C(O)R', —C(S)C(O)R', —C(O)C(S)R', —C(S)C(S)R', —C(O)C(O)OR', —C(S)C(O)OR', —C(O)C(S)OR', —C(O)C(O)SR', —C(S)C(S)OR', —C(S)C(O)SR', —C(O)C(S)SR', —C(S)C(S)SR', —C(O)C(O)N(R')$_2$, —C(S)C(O)N(R')$_2$, —C(O)C(S)N(R')$_2$, or —C(S)C(S)N(R')$_2$;

wherein $R_6$ is in the ortho position and is selected from the group consisting of —CO—NH—(CH$_2$)$_{2-5}$NH$_2$, —CO—NH—(CH$_2$)$_{2-5}$NH—(CH$_2$)$_z$—H, —CO—NH(CH$_2$)$_{2-5}$NR$_{15}$(CH$_2$)$_z$—H, —CO—R', —CO—OR', —CO—SR', —CO—N(R')$_2$, —CO—CO—R', —CO—CS—R', —CO—CO—OR', —CO—CS—OR', —CO—CO—SR', —CO—CS—SR', —CO—CO—N(R')$_2$, —CO—CS—N(R')$_2$, —NH—CO—NH—(CH$_2$)$_{2-5}$NH$_2$, —NH—CO—NH—(CH$_2$)$_{2-5}$NH—(CH$_2$)$_z$—H, —NH—CO—NH(CH$_2$)$_{2-5}$NR$_{15}$(CH$_2$)$_z$—H, —NH—CO—R', —NH—CO—OR', —NH—CO—SR', —NH—CO—NO$_2$, —NH—CO—N(R')$_2$, —NH—CO—CO—R', —NH—CO—CS—R', —NH—CO—CO—OR', —NH—CO—CS—OR', —NH—CO—CO—SR', —NH—CO—CS—SR', —NH—CO—CO—N(R')$_2$, and —NH—CO—CS—N(R')$_2$, wherein each R' is (CH$_2$)$_z$—NR"R" and wherein R" is independently selected from the group consisting of (C$_1$–C$_6$) alkyl, (C$_1$–C$_6$) alkenyl, (C$_1$–C$_6$) alkoxy, (C$_1$–C$_6$) alkynyl, (C$_6$–C$_{20}$) aryl, (C$_6$–C$_{20}$) substituted aryl, (C$_6$–C$_{26}$) alkaryl, substituted (C$_6$–C$_{26}$) alkaryl, and (C$_5$–C$_7$) heteroaryl wherein at least one atom of the heteroaryl is selected from the group consisting of a sulfur, a nitrogen, or an oxygen atom, wherein the aryl and alkaryl substituents are each independently selected from the group consisting of hydrogen, halogen, (C$_1$–C$_6$) alkyl, (C$_1$–C$_6$) alkenyl, (C$_1$–C$_6$) alkynyl and trihalomethyl;

wherein z is 1–6;

wherein $R_{15}$ is selected from the group consisting of halogen, (C$_1$–C$_6$) alkyl, (C$_1$–C$_6$) alkenyl, (C$_1$–C$_6$) alkynyl, and (C$_1$–C$_6$) alkoxy;

wherein X is a group having the following formula;

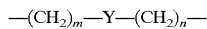
—(CH$_2$)$_m$—Y—(CH$_2$)$_n$— wherein Y is selected from the group consisting of S, N, and O; and wherein m and n, independent of one another, are integers of 0–5.

In a preferred embodiment the compound has the general structural formula:

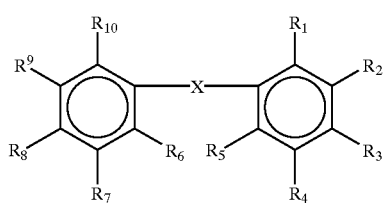

wherein each of the R groups is as defined above.

In another embodiment the compound has the general structural formula:

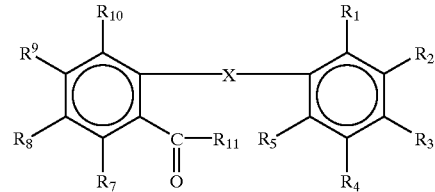

wherein $R_{11}$ is selected from the group consisting of —NH—CH$_2$CH$_2$NH$_2$, —NH—CH$_2$CH$_2$N—(CH$_2$)$_z$—H, —N.(CH$_2$)$_2$N R$_{15}$.(CH$_2$)$_2$, —R', —OR', —SR', —NO$_2$, —N(R')$_2$, —CO—R', —CS—R', —CO—OR', —CS—OR', —CO—SR', —CS—SR', —CO—N(R')$_2$, and —CS—N(R')$_2$ and wherein $R_1$–$R_5$ and $R_7$–$R_{10}$ are as described above.

In yet another embodiment $R_{11}$ is selected from the group consisting of —NH—CH$_2$CH$_2$NH$_2$ and —NH—CH$_2$CH$_2$N—(CH$_2$)$_z$—H and wherein Y is S, m is 0 and n is 1–4.

According to another embodiment the compound has the general structural formula:

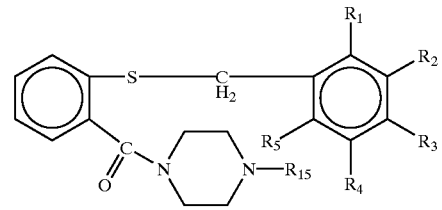

wherein $R_{15}$ is selected from the group consisting of halogen, (C$_1$–C$_6$) alkyl, (C$_1$–C$_6$) alkenyl, (C$_1$–C$_6$) alkynyl, and (C$_1$–C$_6$) alkoxy and wherein $R_1$–$R_5$ are as described above.

According to yet another embodiment the compound has the general structural formula:

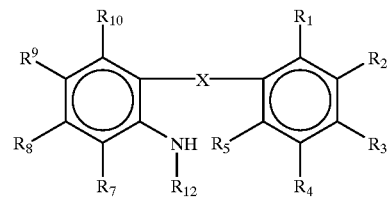

wherein $R_{12}$ is selected from the group consisting of —CO—NH—CH$_2$CH$_2$NH$_2$, —CO—NH—CH$_2$CH$_2$N—(CH$_2$)$_z$—H, and —CO —N.(CH$_2$)$_2$N R$_{15}$.(CH$_2$)$_2$ and wherein $R_1$–$R_5$ and $R_7$–$R_{10}$ are as described above. Preferably, Y is S, m is 0 and n is 1–4. In a more preferred embodiment m is 0 and n is 1–4. In another preferred embodiment Y is S, wherein $R_1$, $R_2$, $R_3$, $R_4$, $R_5$, $R_7$, $R_8$, $R_9$, and $R_{10}$, are H, and wherein $R_6$ is selected from the group consisting of—CO—NH—CH$_2$CH$_2$NH$_2$ and substituted or unsubstituted —CO-piperazine, the substituents selected from the group consisting of —H, halogen, (C$_1$–C$_6$) alkyl, (C$_1$–C$_6$) alkenyl, (C$_1$–C$_6$) alkynyl, and (C$_1$–C$_6$) alkoxy.

A pharmaceutical composition is provided according to another aspect of the invention. The pharmaceutical composition includes a pharmaceutically acceptable carrier and a compound of the invention, as described above, in an amount effective to inhibit calcium channels. In one embodiment the pharmaceutical composition also includes a medicament other than the compound for the treatment of a disorder associated with calcium channel activity. Disorders associated with calcium channel activity include, for example, cardiovascular disease, pulmonary hypertension, peripheral vascular disorder, migraine disorder, mania, epilepsy, depression, hyperuricemia, and asthma (achalasia asthma and bronchial asthma). In one embodiment the medicament for the treatment of cardiovascular disease is a medicament for the treatment of hypertension. In another embodiment the medicament for the treatment of cardiovascular disease is a medicament for the treatment of congestive heart failure. In yet another embodiment the medicament for the treatment of cardiovascular disease is a medicament for the treatment of angina.

According to another aspect of the invention an intermediate in the preparation of the compounds of the invention is provided. The intermediate compound has the general structural formula:

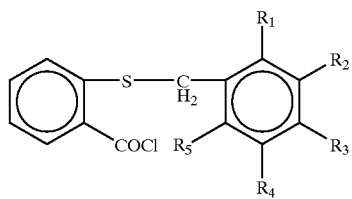

wherein $R_1$, $R_2$, $R_3$, $R_4$, and $R_5$, independent of one another, are selected from the group consisting of hydrogen, halogen, nitro, alkyl, alkoxy or piperonyl.

A method for inhibiting calcium channel activity is provided according to another aspect of the invention. The method involves the step of contacting a cell having a calcium channel with a compound of the invention, as defined above, in an amount effective to inhibit calcium channels.

In another aspect the invention is a method of treating a subject having a disorder associated with calcium channel activity by administering to the subject a compound of the invention, as defined above, in an amount effective to inhibit calcium channels in the subject and a pharmaceutically acceptable carrier. Disorders associated with calcium channel activity include, for example, cardiovascular disease, pulmonary hypertension, peripheral vascular disorder, migraine disorder, mania, epilepsy, depression, hyperuricemia, and asthma (achalasia asthma and bronchial asthma). In one embodiment the subject has a cardiovascular disease. In a preferred embodiment the cardiovascular disease is selected form the group consisting of hypertension, congestive heart failure, arrhythmia, and angina. In other embodiments the subject has a disorder selected from the group consisting of pulmonary hypertension, peripheral vascular disorder, migraine disorder, mania, epilepsy, depression, hyperuricemia, and asthma (achalasia asthma and bronchial asthma).

In one embodiment the method includes the step of administering a medicament other than the compound for the treatment of cardiovascular disease. Preferably the medicament is for treating hypertension. A medicament for treating hypertension in one embodiment is a medicament selected from the group consisting of Ajmaline; γ-Aminobutyric acid; Alfuzosin Hydrochloride; Alipamide; Althiazide; Amiquinsin Hydrochloride; Amlodipine Besylate; Amlodipine Maleate; Amosulalol; Anaritide Acetate; Aryloxypropanolamine derivatives; Atiprosin Maleate; Belfosdil; Bemitradine; Bendacalol Mesylate; Bendroflumethiazide; Benzothiadiazine derivatives; Benzthiazide; Betaxolol Hydrochloride; Bethanidine Sulfate; Bevantolol Hydrochloride; Biclodil Hydrochloride; Bisoprolol; Bisoprolol Fumarate; Bucindolol Hydrochloride; Bupicomide; Bufeniode; Bufuralol; Buthiazide: Candoxatril; Candoxatrilat; Captopril; N-Carboxyalkyl derivatives; Carvedilol; Ceronapril; Chlorothiazide Sodium; Chlorthalidone; Cicletanine; Ciclasidomine; Cilazapril; Clonidine; Clonidine Hydrochloride; Clopamide; Cyclopenthiazide; Cyclothiazide; Cyptenamine tannates; Darodipine; Debrisoquin Sulfate; Delapril Hydrochloride; Diapamide; Diazoxide; Dilevalol Hydrochloride; Diltiazem Malate; Ditekiren; Doxazosin Mesylate; Ecadotril; Enalapril Maleate; Enalaprilat; Enalkiren; Endralazine Mesylate; Epithiazide; Eprosartan; Eprosartan Mesylate; Fenoldopam Mesylate; Flavodilol Maleate; Flordipine; Flosequinan; Fosinopril Sodium; Fosinoprilat; Guanabenz; Guanabenz Acetate; Guanacline Sulfate; Guanadrel Sulfate; Guanazodine; Guancydine; Guanethidine Monosulfate; Guanethidine Sulfate; Guanfacine Hydrochloride; Guanisoquin Sulfate; Guanoclor Sulfate; Guanoctine Hydrochloride; Guanoxabenz; Guanoxan Sulfate; Guanoxyfen Sulfate; Hydralazine Hydrochloride; Hydrazines and phthalazines; Hydralazine Polistirex; Hydroflumethiazide; Imidazole derivatives; Indacrinone; Indapamide; Indolapril Hydrochloride; Indoramin; Indoramin Hydrochloride; Indorenate Hydrochloride; Ketanserin; Labetalol; Lacidipine; Leniquinsin; Levcromakalim; Lisinopril; Lofexidine Hydrochloride; Losartan Potassium; Losulazine Hydrochloride; Mebutamate; Mecamylamine Hydrochloride; Medroxalol; Medroxalol Hydrochloride; Methalthiazide; Methyclothiazide; Methyldopa; Methyldopate Hydrochloride; Methyl 4 pyridyl ketone thiosemicarbarzone; Metipranolol; Metolazone; Metoprolol Fumarate; Metoprolol Succinate; Metyrosine; Minoxidil; Monatepil Maleate; Muzolimine; Nebivolol; Nitrendipine; Ofornine; Pargyline Hydrochloride; Pazoxide; Pelanserin Hydrochloride; Perindopril Erbumine; Pempidine; Piperoxan; primaperone; Protoveratrines; Raubasine; Rescimetol; Rilemenidene; Pronethalol; Phenoxybenzamine Hydrochloride; Pinacidil; Pivopril; Polythiazide; Prazosin Hydrochloride; Primidolol; Prizidilol Hydrochloride; Quaternary Ammonium Compounds; Quinazoline derivatives; Quinapril Hydrochloride; Quinaprilat; Quinazosin Hydrochloride; Quinelorane Hydrochloride; Quinpirole Hydrochloride; Quinuclium Bromide; Ramipril; Rauwolfia Serpentina; Reserpine; Saprisartan Potassium; Saralasin Acetate; Sodium Nitroprusside; Sotalol; Sulfinalol Hydrochloride; Sulfonamide derivatives; Tasosartan; Teludipine Hydrochloride; Temocapril Hydrochloride; Terazosin Hydrochloride; Terlakiren; Tiamenidine; Tiamenidine Hydrochloride; Ticrynafen; Tinabinol; Tiodazosin; Tipentosin Hydrochloride; Trichlormethiazide; Trimazosin Hydrochloride; Trimethaphan Camsylate; Trimoxamine Hydrochloride; Tripamide; Tyrosinase; Urapidil; Xipamide; Zankiren Hydrochloride; and Zofenoprilat Arginine.

In another preferred embodiment the medicament is for treating congestive heart failure. In one embodiment the medicament for treating congestive heart failure is selected from the group consisting of thiazide diuretics, metolazone, furosemide, bumetanide, ethacrynic acid, aldosterone antagonists, trimterene, and amiloride.

In yet another preferred embodiment the medicament is for treating angina. In one embodiment the medicament for treating angina is selected from the group consisting of Acebutolol, Alprenolol, Amiodarone, Arotinolol, Atenolol, Bepridil, Bucumolol, Bufetolol, Bufuralol, Bunitrolol, Bupranolol, Carozolol, Carteolol, Celiprolol, Cinepazet Maleate, Diltiazem, Espanolol, Felodipine, Gallopamil, Imolamine, Indenolol, Isosorbide Dinitrate, Isadipine, Limaprost, Mepindolol, Molsidomine, Nadolol, Nicardipine, Nifedipine, Nifenalol, Nilvadipine, Nipradilol, Nisoldipine, Nitroglycerin, Oxprenolol, Oxyfedrine, Ozagrel, Penbutoolol, Pentaerythritol, Tetranitrate, Pindolol, Pronethalol, Propranolol, Sotaiol, Terodiline, Timolol, Toliprolol; Amlodipine Besylate; Amlodipine Maleate; Betaxolol Hydrochloride; Bevantolol Hydrochloride; Butoprozine Hydrochloride; Carvedilol; Cinepazet Maleate; Metoprolol Succinate; Molsidomine; Monatepil Maleate; Primidolol; Ranolazine Hydrochloride; Tosifen; Verapamil Hydrochloride; and Tirofiban Hydrochloride.

According to another preferred embodiment the medicament is for treating arrhythmia. In one embodiment the medicament for treating arrhythmia is selected from the group consisting of sodium channel blockers such as quinidine, procainamide, disopyramide, moricizine, lidocaine, mexiletine, phenytoin, tocainide, encainide, flecainide, propafenone, indecainide; b-adrenergic blockers, such as propranolol, acebutolol, esmolol; and compounds that prolong repolarization, such as amiodarone, bretylium, sotalol. Other antiarrhythmics include Acebutol, Acecaine, Adenosine, Ajmaline, Alprenolol, Amiodarone, Amoproxan, Aprindine, Arotinolol, Atenolol, Bevantolol, Bretylium Tosylate, Bubumolol, Bufetolol, Bunaftine, Bunitrolol, Bupranolol, Butidrine Hydrochloride, Butobendine, Capobenic Acid, Carazolol, Carteolol, Cifenline, Cloranolol, Gallopamil, Indenolol, Ipratropium Bromide, Lorajmine, Lorcainide, Meobentine, Metipranolol, Mexiletine, Nifenalol, Oxprenolol, Penbutolol, Pindolol, Pirmenol, Practolol, Prajmaline, Pronthalol, Pyrinoline, Quinidine Sulfate, Quinidine, Sotalol, Talinolol, Timolol, Tocainide, Verapamil, Viquidil and Xibenolol.

In one embodiment the administration is per oral. In another embodiment the administration is parenteral. In another embodiment the administration is intravenous.

In yet another aspect of the invention a kit is provided. The kit includes a package housing a container containing the compounds of the invention in an amount effective to inhibit calcium channels and a pharmaceutically acceptable carrier, and instructions for using the compound to treat a subject having a calcium channel blocking disorder.

In one embodiment the kit also includes a second container containing a medicament for the treatment of cardiovascular disease. In this embodiment the instructions are for using the compound and the medicament to treat cardiovascular disease. The medicament for the treatment of cardiovascular disease in some embodiment may be selected from the group consisting of a medicament for the treatment of hypertension, a medicament for the treatment of congestive heart failure, a medicament for the treatment of angina.

In another embodiment the kit also includes a second container containing a medicament for the treatment of a migraine disorder. In this embodiment the instructions are for using the compound and the medicament to treat the migraine disorder.

These and other aspects of the invention are described in greater detail below.

BRIEF DESCRIPTION OF THE DRAWINGS

The present invention may be more easily and completely understood when taken in conjunction with the accompanying drawings.

DETAILED DESCRIPTION OF THE INVENTION

Figure 1:
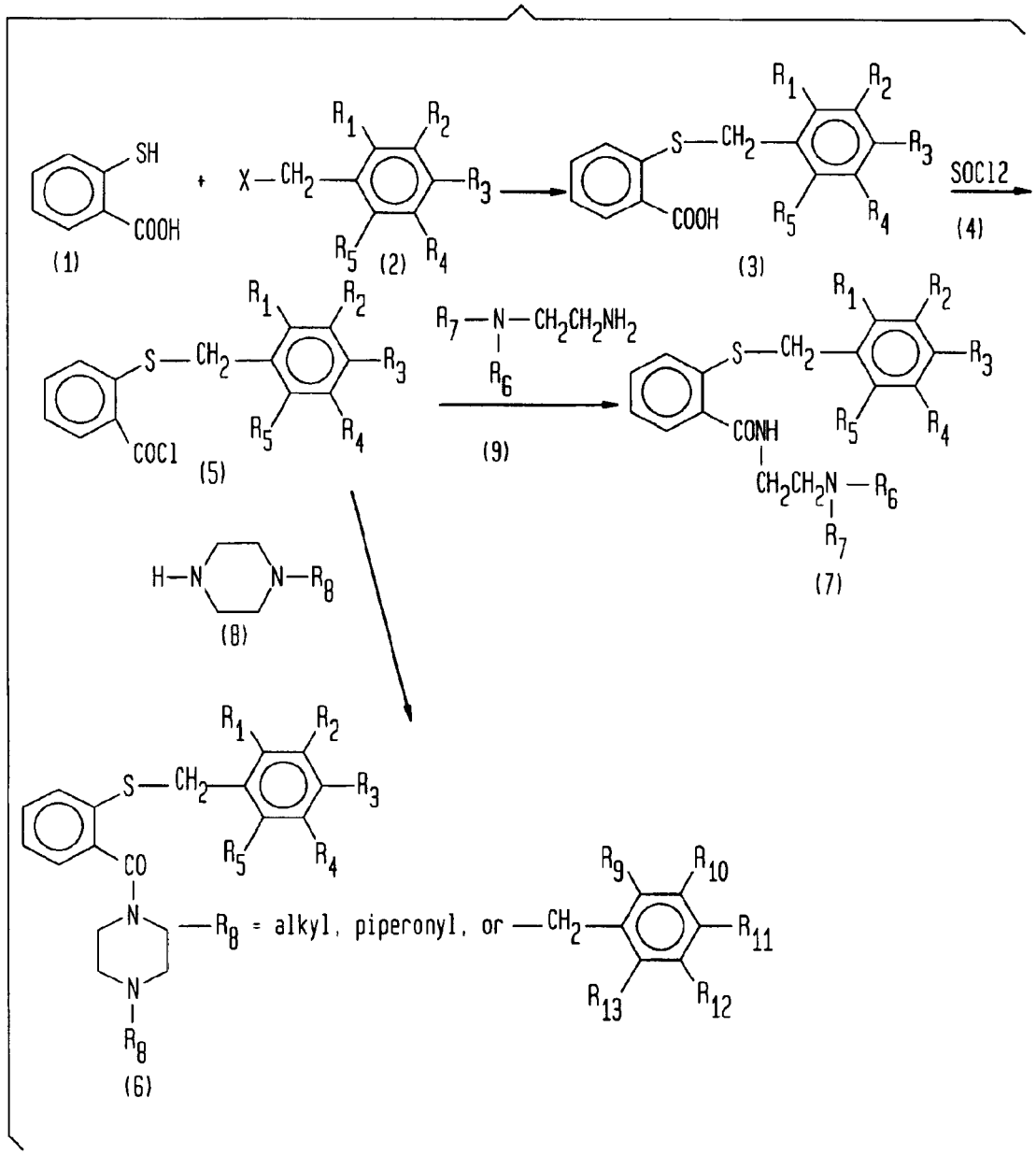
FIG. 1 illustrates the structural formulas of a reaction scheme for a method of synthesizing a compound encompassed by the family of compounds of the invention.
Figure 2:
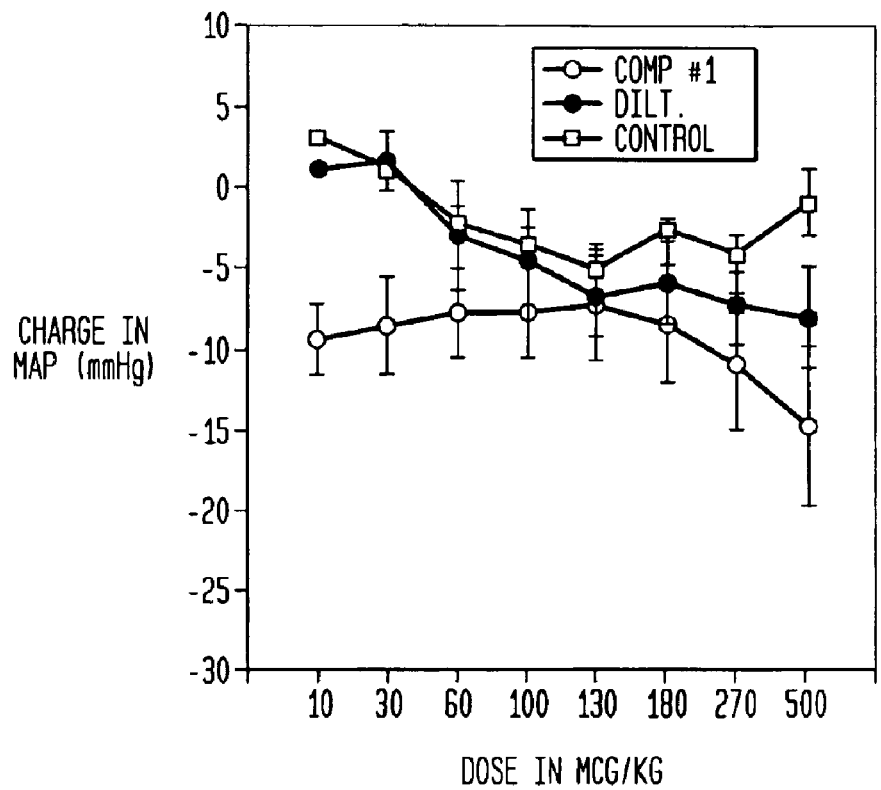
FIG. 2 is a graph depicting the antihypertensive effects of S-(4-methoxybenzyl)-N-(2-(N',N'-dimethylamino)ethyl) thiosalicylamide (an exemplary compound encompassed by the family of compounds of the invention). The test compound and a positive control (Diltiazem) and a negative control were administered to rats in various dosages ranging from 10 to 500 mcg/kg and the maximal arterial blood pressure (MAP) and percent decrease in MAP were determined based on the base line blood pressure.
Figure 3:
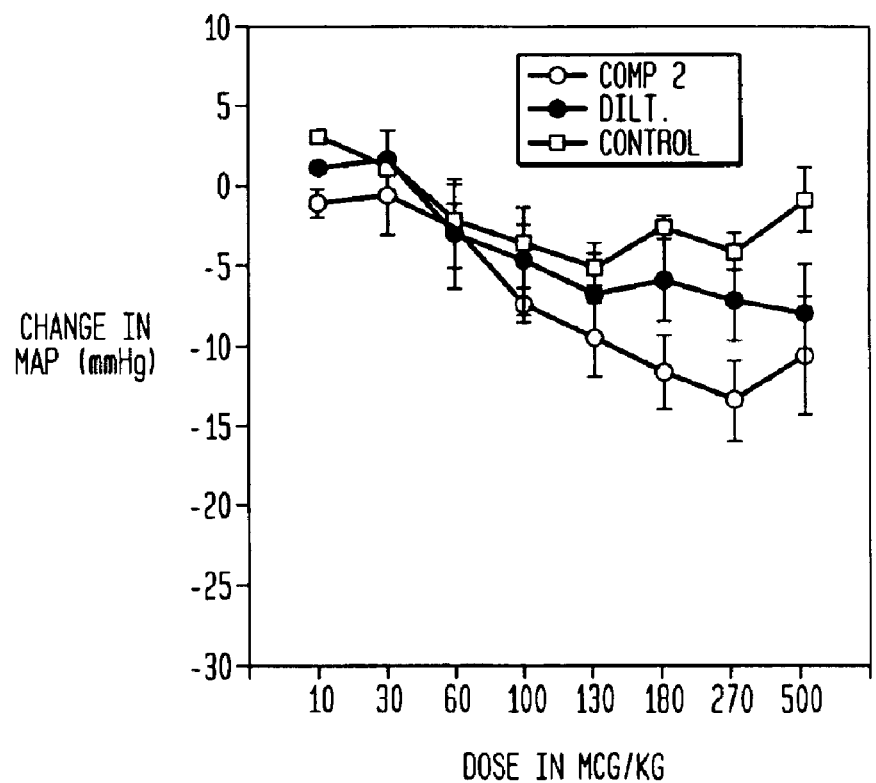
FIG. 3 is a graph depicting the antihypertensive effects of $N^1$-(S-(4-methoxybenzyl) thiosalicyloyl)-$N^4$-methylpiperazine (an exemplary compound encompassed by the family of compounds of the invention). The experimental study was carried out as described in FIG. 2.
Figure 4:
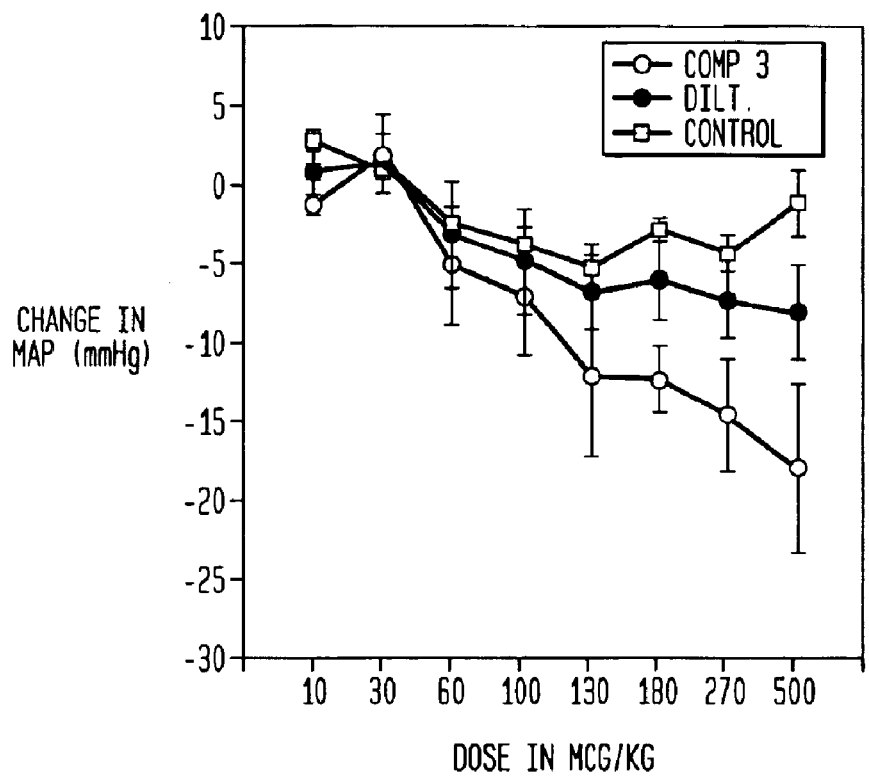
FIG. 4 is a graph depicting the antihypertensive effects of $N^1$-(S-(4'-methoxybenzyl) thiosalicyloyl)-N piperonylpiperazine (an exemplary compound encompassed by the family of compounds of the invention). The experimental study was carried out as described in FIG. 2.
Figure 5:
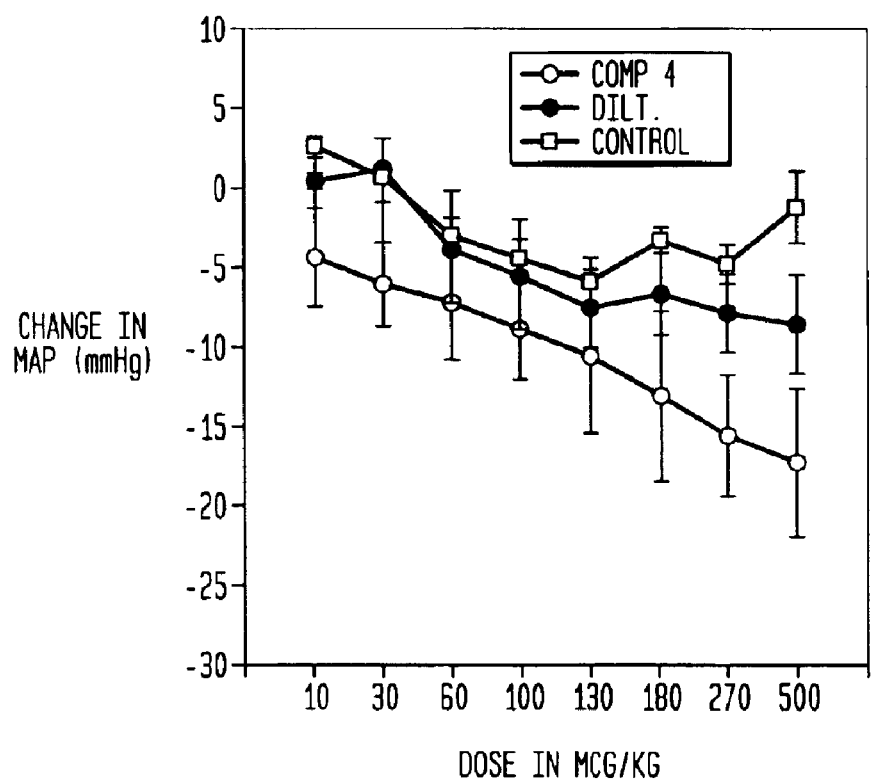
FIG. 5 is a graph depicting the antihypertensive effects of $N^1$-(S-(4-methoxybenzyl) thiosalicyloyl)-N-(4methoxybenzyl)piperazine (an exemplary compound encompassed by the family of compounds of the invention). The experimental study was carried out as described in FIG. 2.
Figure 6:
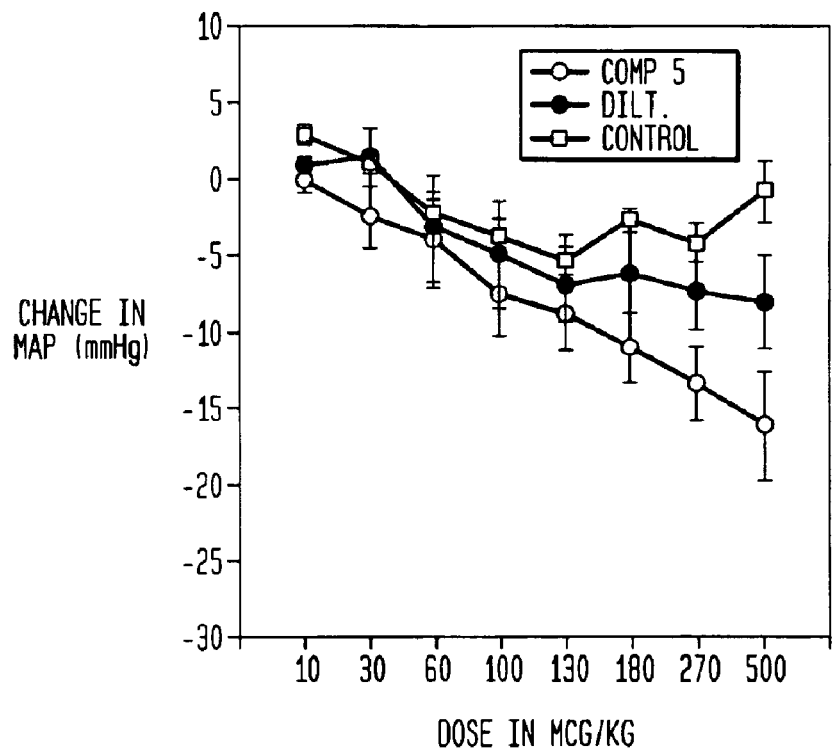
FIG. 6 is a graph depicting the antihypertensive effects of $N^1$-(S-(4-methoxybenzyl)thiosalicyloyl)-$N^4$-benzylpiperazine (an exemplary compound encompassed by the family of compounds of the invention). The experimental study was carried out as described in FIG. 2.

The present invention provides methods and products for inhibiting calcium channel activity. It was found according to the invention that a new family of compounds which have some structural similarity to the benzothiazaepine class of calcium channel blockers have calcium channel blocking activity. The compounds of the invention are distinct from the benzothiazepines because these compounds lack the fused ring structure of benzothiazepines. Previously, it had been believed that the fused ring structure of the benzothiazepines was essential to their activity. Surprisingly, however, it was discovered according to the invention that compounds lacking the fused ring structure actually had comparable calcium channel blocking activity to benzothiazepines such as diltiazem.

Although Applicants do not wish to be bound by a particular mechanism it is believed that the compounds according to the invention and their pharmacologically tolerated salts display their calcium inhibiting activity by influencing the influx of calcium ions into cells through specific channels. The compounds prevent or slow the entry of calcium into the cells by acting on allosteric sites of channel proteins to cause conformational changes which prevent calcium passage rather than simply blocking the channels. The action of these compounds on the calcium channels can be demonstrated using many biochemical test models including the displacement of tritium-labeled diltiazem. In this test, membrane preparations which contain isolated calcium channels are loaded with the labeled diltiazem. After incubation with the test substance, the radioactivity released and the radioactivity remaining on the membrane are determined and the results are reported as an IC50 value.

The compounds useful according to the invention have the following general structural formula:

wherein $Ar_2$ is an aryl group or a heteroaryl group, wherein the heteroaryl is a ring having 5, 6, or 7 atoms, and wherein at least one atom of the heteroaryl is selected from the group consisting of a sulfur, a nitrogen, and an oxygen atom, and which is substituted with $R_1$, $R_2$, $R_3$, $R_4$, and $R_5$;

wherein $Ar_1$ is an aryl group or a heteroaryl group, wherein the heteroaryl is a ring having 5, 6, or 7 atoms, and wherein at least one atom of the heteroaryl is selected from the group consisting of a sulfur, a nitrogen, and an oxygen atom, and which is substituted with $R_6$, $R_7$, $R_8$, $R_9$, and $R_{10}$;

wherein $R_1$, $R_2$, $R_3$, $R_4$, $R_5$, $R_7$, $R_8$, $R_9$, and $R_{10}$ independent of one another, are selected from the group consisting of —H, halogen, piperonyl, $(C_1-C_6)$ alkyl, $(C_1-C_6)$ alkenyl, $(C_1-C_6)$ alkynyl, $(C_1-C_6)$ alkoxy —CN, —OR', —SR', —NO$_2$, —NR'R', amino acid, —C(O)R', —C(S)R', —C(O)OR', —C(S)OR', —C(O)SR, —C(S)SR', —C(O)N(R')$_2$, —C(O)C(O)R', —C(S)C(O)R', —C(O)C(S)R', —C(S)C(S)R', —C(O)C(O)OR', —C(S)C(O)OR', —C(O)C(S)OR', —C(O)C(O)SR', —C(S)C(S)OR', —C(S)C(O)SR', —C(O)C(S)SR', —C(S)C(S)SR', —C(O)C(O)N(R')$_2$, —C(S)C(O)N(R')$_2$, —C(O)C(S)N(R')$_2$, or —C(S)C(S)N(R')$_2$;

wherein $R_6$ is in the ortho position and is selected from the group consisting of —CO—NH—(CH$_2$)$_{2-5}$NH$_2$, —CO—NH—(CH$_2$)$_{2-5}$NH—(CH$_2$)$_z$—H, —CO—NH(CH$_2$)$_{2-5}$NR$_{15}$(CH$_2$)$_z$—H, —CO—R', —CO—OR', —CO—SR', —CO—N(R')$_2$, —CO—CO—R', —CO—CS—R', —CO—CO—OR', —CO—CS—OR', —CO—CO—SR', —CO—CS—SR', —CO—CO—N(R')$_2$, —CO—CS—N(R')$_2$, —NH—CO—NH—(CH$_2$)$_{2-5}$NH$_2$, —NH—CO—NH—(CH$_2$)$_{2-5}$NH—(CH$_2$)$_z$—H, —NH—CO—NH(CH$_2$)$_{2-5}$NR$_{15}$(CH$_2$)$_z$—H, —NH—CO—R', —NH—CO—OR', —NH—CO—SR', —NH—CO—NO$_2$, —NH—CO—N(R')$_2$, —NH—CO—CO—R', —NH—CO—CS—R', —NH—CO—CO—OR', —NH—CO—CS—OR', —NH—CO—CO—SR', —NH—CO—CS—SR', —NH—CO—CO—N(R')$_2$, and —NH—CO—CS—N(R')$_2$, wherein each R' is (CH$_2$)$_z$—NR"R" and wherein R" is independently selected from the group consisting of $(C_1-C_6)$ alkyl, $(C_1-C_6)$ alkenyl, $(C_1-C_6)$ alkoxy, $(C_1-C_6)$ alkynyl, $(C_6-C_{20})$ aryl, $(C_6-C_{20})$ substituted aryl, $(C_6-C_{26})$ alkaryl, substituted $(C_6-C_{26})$ alkaryl, and $(C_5-C_7)$ heteroaryl wherein at least one atom of the heteroaryl is selected from the group consisting of a sulfur, a nitrogen, or an oxygen atom, wherein the aryl and alkaryl substituents are each independently selected from the group consisting of hydrogen, halogen, $(C_1-C_6)$ alkyl, $(C_1-C_6)$ alkenyl, $(C_1-C_6)$ alkynyl and trihalomethyl;

wherein z is 1–6;

wherein $R_{15}$ is selected from the group consisting of halogen, $(C_1-C_6)$ alkyl, $(C_1-C_6)$ alkenyl, $(C_1-C_6)$ alkynyl, and $(C_1-C_6)$ alkoxy;

wherein X is a group having the following formula;

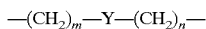

wherein Y is selected from the group consisting of S, N, and O; and wherein m and n, independent of one another, are integers of 0–5.

In one illustrative embodiment of the invention the compounds have the general structural formula:

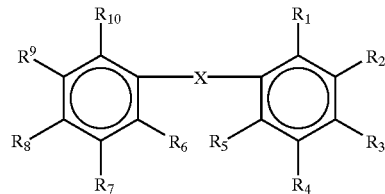

wherein $R_1$–$R_{10}$ are as described above.

In another illustrative embodiment of the invention the compounds have the general structural formula:

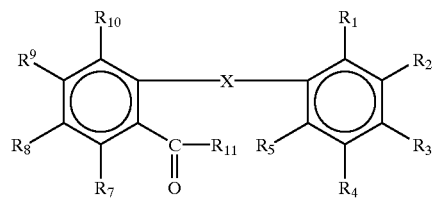

wherein $R_1$–$R_5$ and $R_7$–$R_{10}$ are as described above and wherein $R_{11}$ is selected from the group consisting of —NH—CH$_2$CH$_2$NH$_2$, —NH—CH$_2$CH$_2$N—(CH$_2$)$_z$—H, —N.(CH$_2$)$_2$N R$_{15}$.(CH$_2$)$_2$, R', —OR', —SR', —NO$_2$, —N(R')$_2$, —CO—R', —CS—R', —CO—OR', —CS—OR', —CO—SR', —CS—SR', —CO—N(R')$_2$, and —CS—N(R')$_2$. In preferred embodiments $R_{11}$ is selected from the group consisting of —NH—CH$_2$CH$_2$NH$_2$ and —NH—CH$_2$CH$_2$N—(CH$_2$)$_z$—H and wherein Y is S, m is 0 and n is 1–4.

Exemplary preferred compounds are the following:

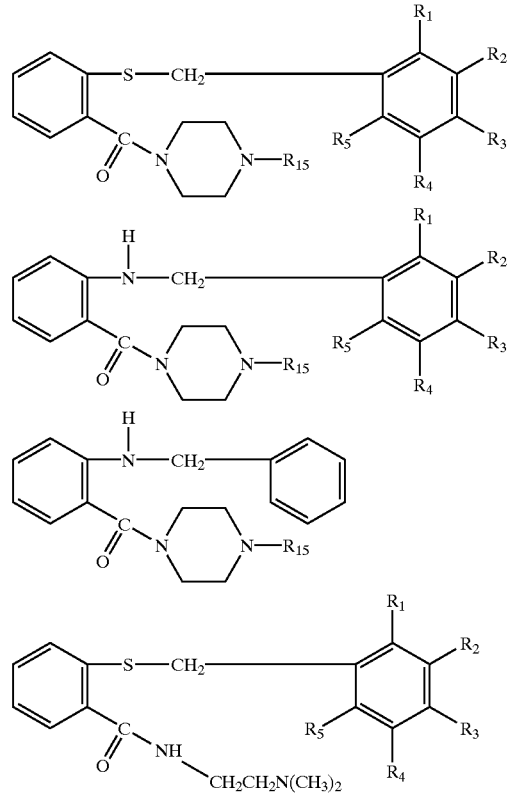

-continued
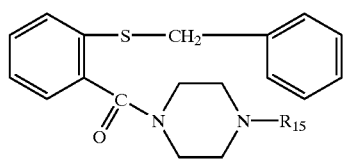
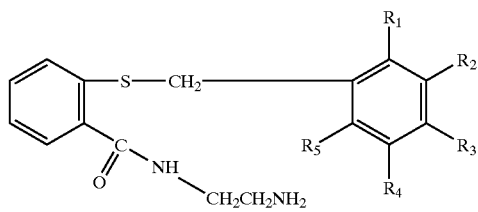
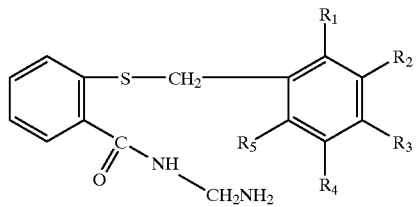
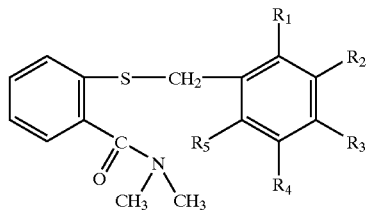
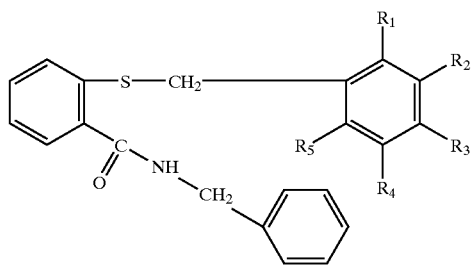
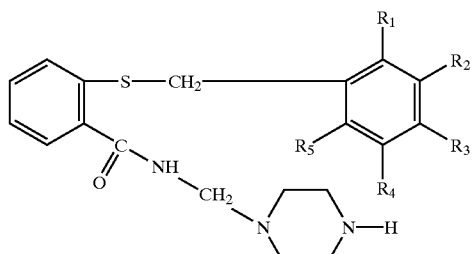
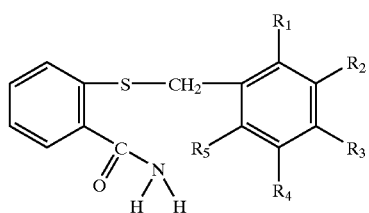
-continued
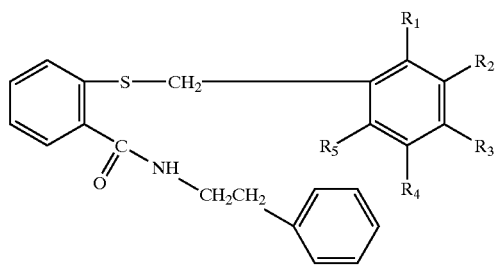
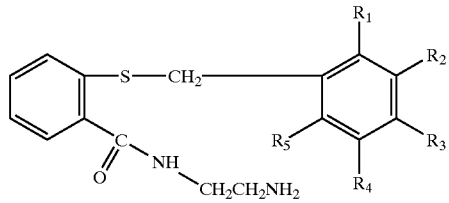
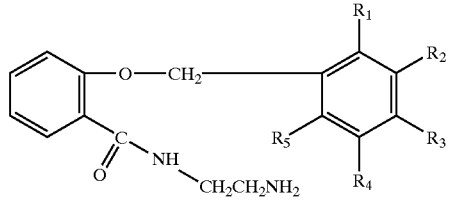
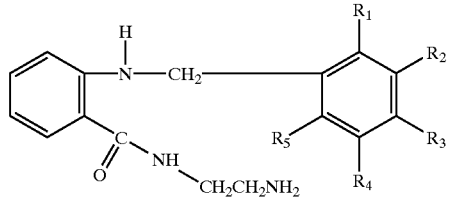
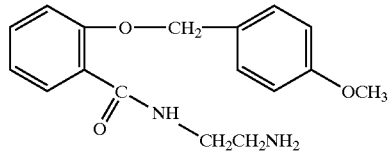
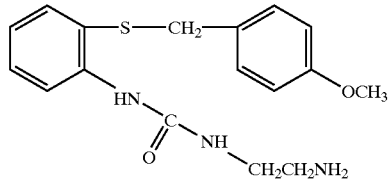
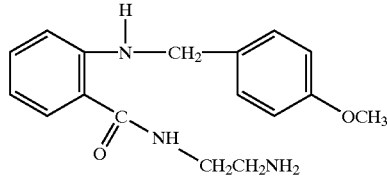
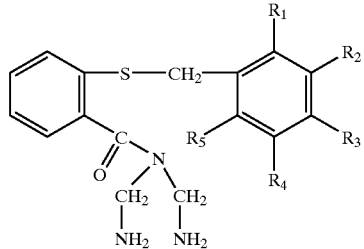

-continued

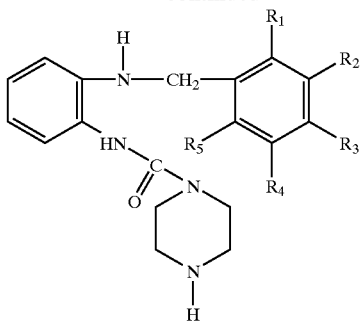

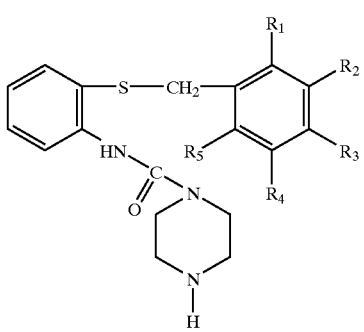

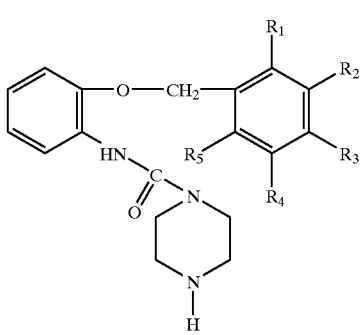

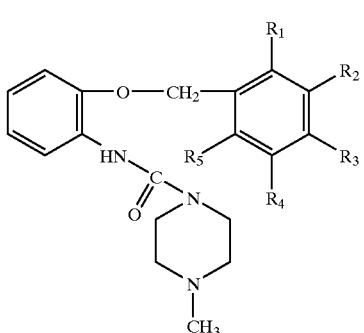

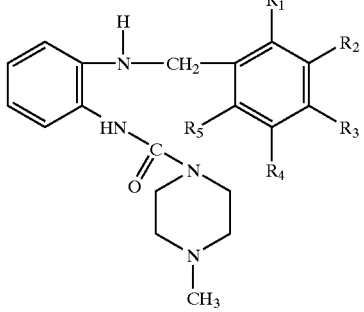

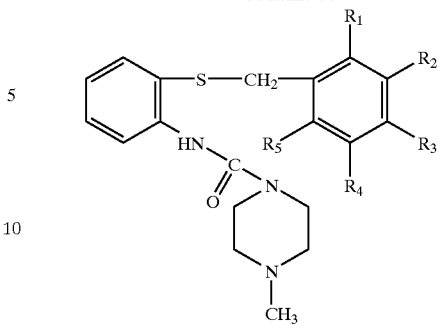

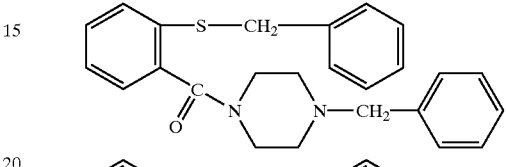

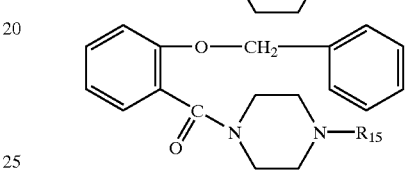

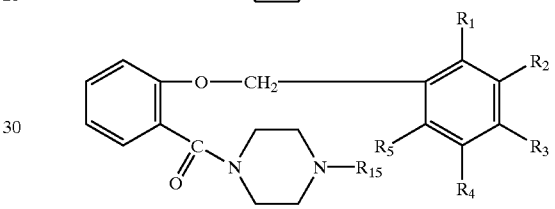

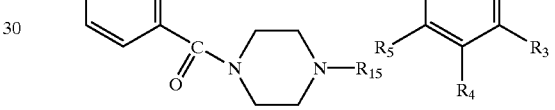

The nomenclature used herein is based on I.U.P.A.C. nomenclature. Throughout this disclosure, the following terms, unless otherwise indicated, shall be understood to have the following meanings:

The term "alkyl" as used in the present description alone—or in combination—denotes straight-chain and branched, saturated aliphatic hydrocarbon residues. Preferred alkyl groups have no more than about 12 carbon atoms and may be methyl, ethyl and structural isomers of propyl, butyl, pentyl, hexyl, heptyl, octyl, nonyl, decyl, undecyl and dodecyl.

"Lower alkyl" means an alkyl group as above, having 1 to about 6 carbon atoms. Examples of lower alkyl-groups are methyl, ethyl, n-propyl, isopropyl, butyl, sec-butyl, tert-butyl, n-pentyl, isopentyl and neopentyl.

The term "alkoxy" denotes an alkyl radical group which is attached to the remainder of the molecule by oxygen.

The term "$C_2$–$C_6$-alkenyl" denotes straight-chain and branched hydrocarbon groups with 2–6 carbon atoms in which at least one carbon-carbon triple bond is unsaturated such as allyl, butenyl and the like.

The term "$C_2$–$C_6$-alkynyl" denotes straight-chain and branched hydrocarbon groups with 2–6 carbon atoms in which at least one carbon-carbon triple bond is present such as propargyl and the like.

The term "halogen" denotes the four halogen atoms fluorine, chlorine, bromine and iodine.

The term "aryl" denotes a mono-aromatic hydrocarbon residue with up to 10 carbon atoms in an aromatic ring structure.

The term "heteroaryl group" embraces 5-, 6 and 7-membered mono- heterocycles which include at least one atom selected from the group consisting of sulfur, oxygen, and nitrogen and which are optionally mono-, di- or tri-substituted by halogen, phenyl, $C_1$–$C_6$-alkyl, $C_3$–$C_6$-alkenyl, $C_3$–$C_6$-alkynyl, $C_1$–$C_6$-alkoxy.

In one aspect of the invention the compounds are present in a pharmaceutical preparation. The pharmaceutical preparations of the invention include pharmaceutically-acceptable amounts and pharmaceutically-acceptable compositions. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, hydriodic, tartaric, lactic, fumaric, oxalic, and the like. Also, pharmaceutically-acceptable salts can be prepared as alkaline metal or alkaline earth salts, such as sodium, potassium or calcium salts. As used herein, a composition of the compounds described above includes salts thereof.

The compounds of the invention may be combined, optionally, with a pharmaceutically-acceptable carrier. The term "pharmaceutically-acceptable carrier" as used herein means one or more compatible solid or liquid filler, diluents or encapsulating substances which are suitable for administration into a human or other animal. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

Pharmaceutical compositions of the invention may be formulated for various administration modes. Carrier formulations suitable for oral, subcutaneous, intravenous, intramuscular, etc. Administrations are described in more detail below and also can be found in Remington, *The Science and Practice of Pharmacy,* Nineteenth Edition, Mack Publishing Company, Eaton, Pa. (1995) which is hereby incorporated by reference.

The pharmaceutical compositions may conveniently be presented in unit dosage form and may be prepared by any of the methods well-known in the art of pharmacy. All methods include the step of bringing the compounds of the invention into association with a carrier which constitutes one or more accessory ingredients. In general, the compositions are prepared by uniformly and intimately bringing the compounds into association with a liquid carrier, a finely divided solid carrier, or both, and then, if necessary, shaping the product.

The compounds of the invention contain at least one asymmetric carbon atom and can therefore exist as enantiomers or diastereomers. The present invention embraces all possible stereoisomers of the compounds of the invention, the pure isomers and all possible diastereoisomeric mixtures and racemates, as well as the separation of these diastereoisomeric mixtures which can be carried out according to known methods. These mixtures of diastereomers can be fractionated into the components by conventional methods, for example selective crystallization from suitable solvents of chromatography on silica gel or aluminum oxide. Customary methods can be used to fractionate the racemates into the individual enantiomers, for example by salt formation with optically active acids, such as camphorsulfonic acid or dibenzoyltartaric acid, and selective crystallization, or by derivatization with suitable optically active reagents, separation of the diastereomeric derivatives and cleavage again. The compounds also include solvated and unsolvated forms.

The foregoing compounds are derived from commercially available products or are synthesized de novo using routine chemical synthetic procedures known to those of ordinary skill in the art. Several examples of chemical synthesis methods are presented in the Examples below.

An exemplary scheme for synthesizing two compounds of the invention is presented in FIG. 1. Thiosalicylic acid (molecule 1) is allowed to interact with substituted-benzyl (molecule 2) to produce S-(substituted-benzyl)thiosalicylic acid (molecule 3). The S-(substituted-benzyl)thiosalicylic acid (molecule 3) is then mixed with sulfonyl chloride (molecule 4) to produce S-(substituted-benzyl)thiosalicyloyl chloride (molecule 5). $N^1$-(S-(substituted-benzyl)thiosalicyloyl)-$N^4$-substituted piperazine (molecule 6) can be prepared by interacting the S-(substituted-benzyl)thiosalicyloyl chloride with $N^4$-substituted piperazine (molecule 8). S-benzyl-N-aminoethylthiosalicylamide (molecule 7) can be prepared from the S-(substituted-benzyl)thiosalicyloyl chloride by the addition of N,N-dimethyl ethylenediamine (molecule 9).

The invention also encompasses a composition of intermediate compound S-(substituted-benzyl)thiosalicyloyl chloride, having the following general structural formula:

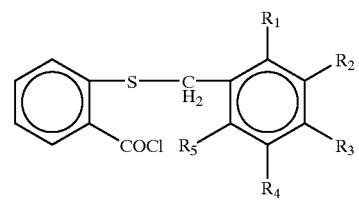

wherein $R_1$, $R_2$, $R_3$, $R_4$, and $R_5$, independent of one another, are selected from the group consisting of hydrogen, halogen, nitro, alkyl, alkoxy or piperonyl constitutes another aspect of the invention. The intermediate compound is useful for preparing the calcium channel blocking compounds of the invention.

The compounds according to the invention, are useful whenever it is desirable to inhibit calcium channel activity in a cell having a calcium channel. It is particularly useful for inhibiting calcium channel activity in situ, and desirably in a subject having a disorder associated with calcium channel activity. By definition, the word "in-situ" encompasses and includes the terms "in-vivo", "ex-vivo" and "in-vitro".

The invention includes a method for inhibiting calcium channel activity by contacting a cell having a calcium channel with a compound of the invention, in an amount effective to inhibit calcium channels. "Inhibiting calcium channels" as used herein refers to the prevention or slowing of calcium entry into a cell through cellular calcium channels. An amount of the compound of the invention which is effective to inhibit calcium channels is that amount sufficient to slow the entry of calcium into a cell by at least 25% as assessed by any in vitro assay used in the art. More preferably the amount effective to inhibit calcium channels is that amount sufficient to slow the entry of calcium into a cell by at least 50%. An exemplary in vitro assay for assessing the rate of calcium entry into a cell is provided in Example 2 below.

Methods for treating a subject in order to inhibit calcium channel activity of the subject are encompassed by the invention. The compounds of the invention in a pharmaceutically acceptable carrier are administered to the subject in an amount effective to inhibit calcium channels in the subject.

The terms "treating" and "treatment" as used herein refer to the treatment of a disorder in a subject, particularly a human, and include: (i) preventing the disorder from occurring in a subject which may be predisposed to the disorder but has not yet been diagnosed as having it; (ii) inhibiting the disorder, i.e., arresting or slowing its development; and/or (iii) relieving the disorder, i.e. causing regression of the disorder.

The compounds of the invention are preferably useful for treating a subject having a disorder associated with calcium channel activity. A "disorder associated with calcium channel activity" as used herein is a physiological malfunction arising from cellular damage and/or cellular death caused by excessive levels of intracellular calcium ions. Such disorders include, for example, but are not limited to cardiovascular disease, pulmonary hypertension, peripheral vascular disorder, migraine disorder, mania, epilepsy, depression, hyperuricemia, and asthma (achalasia asthma and bronchial asthma). See, e.g., Harrisons, Principles of Internal Medicine (McGraw Hill, Inc., New York) for a more detailed description of each of these conditions.

The term "subject" as used herein, is intended to mean humans, primates, horses, cows, swine, goats, sheep, dogs, and cats.

A "cardiovascular disease" as used herein is a disease of the heart and/or blood vessels caused by high levels of calcium ions within the cardiac tissue. Preferably the cardiovascular disease is selected form the group consisting of hypertension, congestive heart failure, arrhythmia, and angina.

A "subject having hypertension" is a subject who has a disorder involving elevated arterial pressure. A "subject at risk of developing hypertension" is a subject who has a propensity of developing hypertension because of certain factors affecting the cardiovascular system of the subject. Factors which influence the development of hypertension include but are not limited to exposure to environmental factors such as high salt intake, occupation, and alcohol; as well as obesity and heredity. It is desirable to reduce the risk in these subjects of developing hypertension. Reducing the risk of hypertension includes a slowing of the progression towards hypertension or preventing the development of hypertension.

A "subject having congestive heart failure" is a subject who has a disorder involving a clinical syndrome of diverse etiologies linked by the common denominator of impaired heart pumping in which the heart cannot pump blood commensurate with the requirements of the metabolizing tissues, or can do so only from an elevated filling pressure. A "subject at risk of developing congestive heart failure" is a subject who has a propensity of developing congestive heart failure because of certain factors affecting the cardiovascular system of the subject. It is desirable to reduce the risk in these subjects of developing congestive heart failure.

A "subject having arrhythmia" is a subject who has a disorder involving a variation from the normal rhythm of the heart beat. Arrhythmia may arise as a result of altered normal automaticity of impulse generation, abnormal generation of impulses, and abnormalities of impulse conduction. A "subject at risk of developing arrhythmia" is a subject who has a propensity of developing arrhythmia because of certain factors affecting the cardiovascular system of the subject. Factors which influence the development of arrhythmia include but are not limited to acute infections, such as viral myocarditis, acute rheumatic fever, Lyme disease, and degenerative diseases, as a result of interruption of the blood supply to the sinus node. It is desirable to reduce the risk in these subjects of developing arrhythmia.

The term "angina" as used herein refers to either variant angina or exertional angina as those terms are defined in the Seventh edition of Goodman and Gilman's, *The Pharmacological Basis of Therapeutics*. A "subject having angina" is a subject having ischemic heart disease which is manifested by sudden, severe, pressing substernal pain that often radiates to the left shoulder and along the left arm.

Pulmonary hypertension is a disease characterized by increased pulmonary arterial pressure and pulmonary vascular resistance of the vessels, as well as vascular remodeling which leads to narrowed lumens of the vessels. Pulmonary hypertension can be primary, i.e. of unknown or unidentifiable cause, or can be secondary to a known cause such as hypoxia or congenital heart shunts. The term "primary pulmonary hypertension" generally refers to a condition in which there is elevated arterial pressures in the small pulmonary arteries. Pulmonary hypertension generally occurs independently of and is unrelated to systemic hypertension. In vitro studies have concluded that changes in Ca++ concentrations may be involved in pulmonary tissue damage associated with pulmonary hypertension. Farruck et al., *Am. Rev. Respir. Dis.*, v. 145, No. 6, p. 1389–97 (1992). A subject having pulmonary hypertension as used herein is a subject having a right ventricular systolic or a pulmonary artery systolic pressure, at rest, of at least 20 mmHg. Pulmonary hypertension is measured using conventional procedures well-known to those of ordinary skill in the art.

A subject at risk of developing pulmonary hypertension may be treated prophylactically to reduce the risk of pulmonary hypertension. A subject with an abnormally elevated risk of pulmonary hypertension is a subject with chronic exposure to hypoxic conditions, a subject with sustained vasoconstriction, a subject with multiple pulmonary emboli, a subject with cardiomegaly and/or a subject with a family history of pulmonary hypertension.

"Peripheral vascular disorder" is a disorder caused by segmental lesions arising from stenosis or occlusion of large and medium size blood vessels, and most often occurs in the upper extremities.

A "migraine disorder" as used herein is a disorder which involves complex periodic attacks of vascular headache. Vascular headache is generally temporal or unilateral in onset. Migraines are generally familial and often are triggered by factors such as diet, alcohol, chocolate, coffee, exposure to sunlight, exercise, tension, or the use of oral contraceptives, or physiological changes such as occur during the menstrual cycle. No one biochemical mechanism has been identified yet which appears to be responsible for causing migraines. The predominate belief expressed in the literature is that vasodilation of extracranial vessels causes migraine. Many treatment efforts, therefore, have aimed at methods of causing vasoconstriction. More recently, evidence has shown that activation of prejunctional 5-HT$_1$ heteroreceptors on primary afferent trigeminovascular fibers, by drugs such as ergot alkaloids and sumatriptan, alleviate migraine pain, suggesting a neuronal pathogenesis as opposed to a vascular one.

Mania, often seen in conjunction with depression in the bipolar disorder of manic-depressive illness, is characterized by a display of symptoms such as euphoria, increased psycho-motor activity, rapid speech, flight of ideas, decreased need for sleep, distractability, grandiosity and poor judgment.

Epilepsy is a disorder characterized by chronic recurrent paroxysmal changes in neurologic function which is caused by abnormalities in the electrical activity of the brain. Epilepsy may arise as a result of neurologic injury, anoxia or ischemia before or during birth, a structural brain lesion, other systemic medical diseases, such as hypoglycemia, hypocalcemia, hypomagnesemia, and infections, or genetics.

Depression also known as major depressive disorder is a mood disorder of unknown cause. Genetic factor, neurotransmitter dysregulation, environmental factors, brain-environmental interactions and biological rhythms have all been suggested potential contributors to the cause of depression.

Hyperuricemia as used herein is a disorder characterized by excessive plasma or serum concentrations of urate. Ordinarily a subject having concentrations of urate in the plasma of greater than 420 mmol/L (7.0 mg/dL) is said to have clinical hyperuricemia. Hyperuricemia may result from either an increases urate production (often caused by high levels of exogenous purines in the diet or increases in endogenous production), decreased uric acid excretion (e.g., decreased glomerular filtration, decreased tubular secretion, or enhanced tubular reabsorption) or a combination of the two.

Asthma is a disease of the airways which is characterized by increased responsiveness of the tracheobronchial tissue to stimulants resulting in narrowing of the air passages. Asthma attacks are triggered by allergens, pharmacologic stimuli, environment and air pollution, occupational factors, infections, exercise and emotional stress.

The compounds of the invention are administered in effective amounts. In general an effective amount is that amount sufficient to produce a medically desirable result (e.g. an antihypertensive amount, anti-anginal amount, anti-manic amount, etc.). Effective amounts will depend, of course, on the particular condition being treated; the severity of the condition, individual patient parameters including age, physical condition, size and weight, the duration of the treatment, the nature of the concurrent therapy (if any), the specific route of administration and like factors within the knowledge and expertise of the health practitioner. These factors are well known to those of ordinary skill in the art and can be addressed with no more than routine experimentation. For example, an amount effective for treating hypertension would be an amount sufficient to reduce the arterial blood pressure so as to achieve a diastolic pressure of approximately 82 mmHg or less and a systolic pressure of approximately 130 mmHg or less. It will be understood that the compounds of the invention can be used to treat hypertension prophylactically in subjects at risk of developing hypertension as well as in subjects having hypertension.

Generally, systemic doses of active compounds will be from about 0.01 milligrams/kg body weight per day to 10 milligrams/kg body weight per day. It is expected that oral doses in the range of 0.1 to 100 milligrams/kg body weight, in one or several administrations per day, will yield the desired results. The dose for intravenous and intramuscular administration generally ranges between 1 to 300 mg, and preferably 5 to 150 mg, a day. In the event that the response in a subject is insufficient at such doses, even higher doses (or effective higher doses by a different, more localized delivery route) may be employed to the extent that patient tolerance permits. In the event that lower doses are sufficient to improve disorders associated with calcium channel activity, lower doses may be employed. Multiple doses per day are contemplated to achieve appropriate systemic levels of compounds. In one embodiment a maximal dose is administered first, followed by submaximal dosages.

Optionally, the compounds of the invention are administered to the subject in combination with a method for treating a disorder associated with calcium channel activity. The method for treating the disorder associated with calcium channel activity may be a surgical method, a method involving a drug therapy (e.g., a pharmaceutical, gene therapy, etc.) or a combination of the foregoing. Drug therapies which are useful for treating the disorder include but are not limited to antihypertensives, anti-anginal drugs, anti-arrhythmia drugs, drugs for the treatment of congestive heart failure, anti-migraine drugs, anti-epileptic drugs, antidepressants, anti-asthmatics, drugs for the treatment of hyperuricemia, and drugs for the treatment of peripheral vascular disorder.

Antihypertensives include but are not limited to Ajmaline; g-Aminobutyric acid; Alfuzosin Hydrochloride; Alipamide; Althiazide; Amiquinsin Hydrochloride; Amlodipine Besylate; Amlodipine Maleate; Amosulalol; Anaritide Acetate; Aryloxypropanolamine derivatives; Atiprosin Maleate; Belfosdil; Bemitradine; Bendacalol Mesylate; Bendroflumethiazide; Benzothiadiazine derivatives; Benzthiazide; Betaxolol Hydrochloride; Bethanidine Sulfate; Bevantolol Hydrochloride; Biclodil Hydrochloride; Bisoprolol; Bisoprolol Fumarate; Bucindolol Hydrochloride; Bupicomide; Bufeniode; Bufuralol; Buthiazide: Candoxatril; Candoxatrilat; Captopril; N-Carboxyalkyl derivatives; Carvedilol; Ceronapril; Chlorothiazide Sodium; Chlorthalidone; Cicletanine; Ciclasidomine; Cilazapril; Clonidine; Clonidine Hydrochloride; Clopamide; Cyclopenthiazide; Cyclothiazide; Cyptenamine tannates; Darodipine; Debrisoquin Sulfate; Delapril Hydrochloride; Diapamide; Diazoxide; Dilevalol Hydrochloride; Diltiazem Malate; Ditekiren; Doxazosin Mesylate; Ecadotril; Enalapril Maleate; Enalaprilat; Enalkiren; Endralazine Mesylate; Epithiazide; Eprosartan; Eprosartan Mesylate; Fenoldopam Mesylate; Flavodilol Maleate; Flordipine; Flosequinan; Fosinopril Sodium; Fosinoprilat; Guanabenz; Guanabenz Acetate; Guanacline Sulfate; Guanadrel Sulfate; Guanazodine; Guancydine; Guanethidine Monosulfate; Guanethidine Sulfate; Guanfacine Hydrochloride; Guanisoquin Sulfate; Guanoclor Sulfate; Guanoctine Hydrochloride; Guanoxabenz; Guanoxan Sulfate; Guanoxyfen Sulfate; Hydralazine Hydrochloride; Hydrazines and phthalazines; Hydralazine Polistirex; Hydroflumethiazide; Imidazole derivatives; Indacrinone; Indapamide; Indolapril Hydrochloride; Indoramin; Indoramin Hydrochloride; Indorenate Hydrochloride; Ketanserin; Labetalol; Lacidipine; Leniquinsin; Levcromakalim; Lisinopril; Lofexidine Hydrochloride; Losartan Potassium; Losulazine Hydrochloride; Mebutamate; Mecamylamine Hydrochloride; Medroxalol; Medroxalol Hydrochloride; Methalthiazide; Methyclothiazide; Methyldopa; Methyldopate Hydrochloride; Methyl 4 pyridyl ketone thiosemicarbarzone; Metipranolol; Metolazone; Metoprolol Fumarate; Metoprolol Succinate; Metyrosine;

Minoxidil; Monatepil Maleate; Muzolimine; Nebivolol; Nitrendipine; Ofornine; Pargyline Hydrochloride; Pazoxide; Pelanserin Hydrochloride; Perindopril Erbumine; Pempidine; Piperoxan; primaperone; Protoveratrines; Raubasine; Rescimetol; Rilemenidene; Pronethalol; Phenoxybenzamine Hydrochloride; Pinacidil; Pivopril; Polythiazide; Prazosin Hydrochloride; Primidolol; Prizidilol Hydrochloride; Quaternary Ammonium Compounds; Quinazoline derivatives; Quinapril Hydrochloride; Quinaprilat; Quinazosin Hydrochloride; Quinelorane Hydrochloride; Quinpirole Hydrochloride; Quinuclium Bromide; Ramipril; Rauwolfia Serpentina; Reserpine; Saprisartan Potassium; Saralasin Acetate; Sodium Nitroprusside; Sotalol; Sulfinalol Hydrochloride; Sulfonamide derivatives; Tasosartan; Teludipine Hydrochloride; Temocapril Hydrochloride; Terazosin Hydrochloride; Terlakiren; Tiamenidine; Tiamenidine Hydrochloride; Ticrynafen; Tinabinol; Tiodazosin; Tipentosin Hydrochloride; Trichlormethiazide; Trimazosin Hydrochloride; Trimethaphan Camsylate; Trimoxamine Hydrochloride; Tripamide; Tyrosinase; Urapidil; Xipamide; Zankiren Hydrochloride; and Zofenoprilat Arginine.

Anti-anginal drugs include but are not limited to Acebutolol, Alprenolol. Amiodarone, Arotinolol, Atenolol, Bepridil, Bucumolol, Bufetolol, Bufuralol, Bunitrolol, Bupranolol, Carozolol, Carteolol, Celiprolol, Cinepazet Maleate, Diltiazem, Espanolol, Felodipine, Gallopamil, Imolamine, Indenolol, Isosorbide Dinitrate, Isadipine, Limaprost, Mepindolol, Molsidomine, Nadolol, Nicardipine, Nifedipine, Nifenalol, Nilvadipine, Nipradilol, Nisoldipine, Nitroglycerin, Oxprenolol, Oxyfedrine, Ozagrel, Penbutoolol, Pentaerythritol, Tetranitrate, Pindolol, Pronethalol, Propranolol, Sotaiol, Terodiline, Timolol, Toliprolol; Amlodipine Besylate; Amlodipine Maleate; Betaxolol Hydrochloride; Bevantolol Hydrochloride; Butoprozine Hydrochloride; Carvedilol; Cinepazet Maleate; Metoprolol Succinate; Molsidomine; Monatepil Maleate; Primidolol; Ranolazine Hydrochloride; Tosifen; Verapamil Hydrochloride; and Tirofiban Hydrochloride.

Anti-arrhythmia drugs include but are not limited to sodium channel blockers such as quinidine, procainamide, disopyramide, moricizine, lidocaine, mexiletine, phenytoin, tocainide, encainide, flecainide, propafenone, indecainide; b-adrenergic blockers, such as propranolol, acebutolol, esmolol; and compounds that prolong repolarization, such as amiodarone, bretylium, sotalol. Other antiarrhythmics include Acebutol, Acecaine, Adenosine, Ajmaline, Alprenolol, Amiodarone, Amoproxan, Aprindine, Arotinolol, Atenolol, Bevantolol, Bretylium Tosylate, Bubumolol, Bufetolol, Bunaftine, Bunitrolol, Bupranolol, Butidrine Hydrochloride, Butobendine, Capobenic Acid, Carazolol, Carteolol, Cifenline, Cloranolol, Gallopamil, Indenolol, Ipratropium Bromide, Lorajmine, Lorcainide, Meobentine, Metipranolol, Mexiletine, Nifenalol, Oxprenolol, Penbutolol, Pindolol, Pirmenol, Practolol, Prajmaline, Pronthalol, Pyrinoline, Quinidine Sulfate, Quinidine, Sotalol, Talinolol, Timolol, Tocainide, Verapamil, Viquidil and Xibenolol.

Drugs for the treatment of congestive heart failure include but are not limited to thiazide diuretics, metolazone, furosemide, bumetanide, ethacrynic acid, aldosterone antagonists, trimterene, and amiloride.

Anti-migraine drugs include but are not limited to Aliliropride; Dihydroergotamine; propanolol; methysergide; tricyclic antidepressants; aspirin like-drugs; ergotamine; ergot alkaloids; valproate; stadol; Dolasetron Mesylate; Ergocornine, Ergocorninine; Ergocryptine; Ergot; Ergotamine; Flumedroxone acetate; Fonazine; Lisuride; Methysegide; Naratriptan Hydrochloride; Oxetorpne; Pexotyline; Sergolexole Maleate; Sumatriptan Succinate; and Zatosetron Maleate.

Anti-epileptic drugs include but are not limited to Felbamate; Loreclezole; and Tolgabide.

Antidepressants include but are not limited to Amitriptylinoxide, Demexiptiline, Dibenzepin, Dimetracrine, Fluacizine, Imipramine N-Oside, Metapramine, Noxiptilin, Quinupramine, Tianeptine; Adrafinil, Benactyzine, Deanol, Deanol Aceglumate, Deanol Acetamidobenzoate, Etoperidone, Febarbamate, Femoxetine, Fenpentadiol, Fluvoxamine, Hematoporphyrin, Hypercinin, Levophacetoperane, Medifoxamine, Oxaflozane, Piberaline, Pyrisuccideanol, Rubidium Chloride, Sultopride, Teniloxazine, Tofenacin, Toloxatone, Tranylcypromine, L-Tryptophan and Zimeldine Adatanserin Hydrochloride; Adinazolam; Adinazolam Mesylate; Alaproclate; Aletamine Hydrochloride; Amedalin Hydrochloride; Amitriptyline Hydrochloride; Amoxapine; Aptazapine Maleate; Azaloxan Fumarate; Azepindole; Azipramine Hydrochloride; Bipenamol Hydrochloride; Bupropion Hydrochloride; Butacetin; Butriptyline Hydrochloride; Caroxazone; Cartazolate; Ciclazindol; Cidoxepin Hydrochloride; Cilobamine Mesylate; Clodazon Hydrochloride; Clomipramine Hydrochloride; Cotinine Fumarate; Cyclindole; Cypenamine Hydrochloride; Cyprolidol Hydrochloride; Cyproximide; Daledalin Tosylate; Dapoxetine Hydrochloride; Dazadrol Maleate; Dazepinil Hydrochloride; Desipramine Hydrochloride; Dexamisole; Deximafen; Dibenzepin Hydrochloride; Dioxadrol Hydrochloride; Dothiepin Hydrochloride; Doxepin Hydrochloride; Duloxetine Hydrochloride; Eclanamine Maleate; Encyprate; Etoperidone Hydrochloride; Fantridone Hydrochloride; Fenmetozole Hydrochloride; Fenmetramide; Fezolamine Fumarate; Fluotracen Hydrochloride; Fluoxetine; Fluoxetine Hydrochloride; Fluparoxan Hydrochloride; Gamfexine; Guanoxyfen Sulfate; Imafen Hydrochloride; Imiloxan Hydrochloride; Imipramine Hydrochloride; Indeloxazine Hydrochloride; Intriptyline Hydrochloride; Iprindole; Isocarboxazid; Ketipramine Fumarate; Lofepramine Hydrochloride; Lortalamine; Maprotiline; Maprotiline Hydrochloride; Melitracen Hydrochloride; Milacemide Hydrochloride; Minaprine Hydrochloride; Mirtazapine; Moclobemide; Modaline Sulfate; Napactadine Hydrochloride; Napamezole Hydrochloride; Nefazodone Hydrochloride; Nisoxetine; Nitrafudam Hydrochloride; Nomifensine Maleate; Nortriptyline Hydrochloride; Octriptyline Phosphate; Opipramol Hydrochloride; Oxaprotiline Hydrochloride; Oxypertine; Paroxetine; Phenelzine Sulfate; Pirandamine Hydrochloride; Pizotyline; Pridefine Hydrochloride; Prolintane Hydrochloride; Protriptyline Hydrochloride; Quipazine Maleate; Rolicyprine; Seproxetine Hydrochloride; Sertraline Hydrochloride; Sibutramine Hydrochloride; Sulpiride; Suritozole; Tametraline Hydrochloride; Tampramine Fumarate; Tandamine Hydrochloride; Thiazesim Hydrochloride; Thozalinone; Tomoxetine Hydrochloride; Trazodone Hydrochloride; Trebenzomine Hydrochloride; Trimipramine; Trimipramine Maleate; Venlafaxine Hydrochloride; Viloxazine Hydrochloride; Zimeldine Hydrochloride; and Zometapine.

Anti-asthmatics include but are not limited to Ablukast; Ablukast Sodium; Azelastine Hydrochloride; Bunaprolast; Cinalukast; Cromitrile Sodium; Cromolyn Sodium; Enofelast; Isamoxole; Ketotifen Fumarate; Levcromakalim; Lodoxamide Ethyl; Lodoxamide Tromethamine; Montelukast Sodium; Ontazolast; Oxarbazole; Oxatomide; Piriprost; Piriprost Potassium; Pirolate; Pobilukast Edamine;

Quazolast; Repirinast; Ritolukast; Sulukast; Tetrazolast Meglumine; Tiaramide Hydrochloride; Tibenelast Sodium; Tomelukast; Tranilast; Verlukast; Verofylline; Zarirlukast.

Drugs for the treatment of hyperuricemia include but are not limited to allopurinol and uricosuric agents.

Drugs for the treatment of peripheral vascular disorder include but are not limited to heparin, pentoxifylline, thrombolytic drugs, and vasodilators.

The above-described drug therapies are well known to those of ordinary skill in the art and are administered by modes know to those of skill in the art. The combined drug therapies are administered in amounts which are effective to achieve the physiological goals (to improve the disorder, e.g., reduce hypertension), in combination with the compounds of the invention. Thus, it is contemplated that the drug therapies may be administered in amounts which are not capable of improving the disorder when the drug therapies are administered alone but which are capable of improving the disorder when administered in combination with the compounds of the invention.

When administered the compounds of the invention are administered wither per se or in pharmaceutically acceptable carriers using a variety of administration routes. The particular mode selected will depend of course, upon the particular drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, bronchial, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule.

Compositions suitable for oral administration may be presented as discrete units, such as capsules, tablets, lozenges, pills, liquids, cachets, dragees, gels, lactose maize starch or derivatives thereof, talc, stearic acid, or its salts and the like each containing a predetermined amount of the active compounds. Other compositions include suspensions in aqueous liquids or non-aqueous liquids such as a syrup, elixir or an emulsion.

A tablet is a solid pharmaceutical dosage form containing a drug substance prepared either by compression or molding methods. The tablet may optionally include suitable diluents, additives, or excipients. Tablets may be of any shape or size which can be orally ingested. For instance, tablets may be discoid, round, oval, oblong, cylindrical, or triangular.

A gelatin capsule is a solid dosage form having a drug substance enclosed either in a hard or soft soluble container or shell made of a suitable form of gelatin. The hard gelatin capsule which is also referred to as the dry-filled capsule consists of two sections, one of which slips ver the other to completely surround the drug formulation. Soft gelatin capsules include glycerin, sorbitol or a similar polyol for produce a soft globular gelatin shell which can be filled with a drug.

Lozenges also known as pastilles or troches are generally discoid shaped solid materials which contain the drug and the a suitably flavored base. Lozenges are placed in the oral cavity and allowed to slowly dissolve in order to deliver the drug.

Cachets are a capsule like container having a drug encapsulated in a shell. The drug is placed into the two halves of the shell and the edges of the two halves are sealed to produce a the sealed capsule like container.

Dragees are a coated form of tablet. The dragee core is coated with flavoring solution such as concentrated sugar solutions which may optionally contain gum arabic, talc, polyvinyl, pyrrolidone, carbopol, gel, polyethylene glycol, and/or titanium dioxide, lacquer solutions, and suitable organic solvents or solvent mixtures. The dragee coatings may also contain dyestuffs or pigments.

Compositions suitable for rectal administration include suppository bases and retention enemas which include for example, natural or hardened oils, waxes, fats, semi-liquid polyols and the like.

Compositions suitable for parenteral administration conveniently comprise a sterile aqueous preparation of the compounds of the invention, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables.

Compositions suitable for buccal administration may take the form of tablets, lozenges, etc.

Topical formulations include the drug of interest in a cream, lotion, gel, transdermal patch or powdered form. Optionally the topical formulations may include permeation enhancers that are useful for enhancing the uptake of the drug through the skin. Permeation enhancers are well known in the art and are commercially available.

Compositions suitable for nasal or bronchial administration include emulsions for aerosol delivery. In general an aerosol is a finely dispersed mist, foam, or semisolid material which is delivered to the nose or mouth as a spray powered by a liquefied or compressed gas or a pump. Aerosols sprays may be delivered in a pressurized pack or nebulizer with the use of a propellant, such as fluorocarbon propellants (e.g., dichlorodifluoromethane, trichlorofluoromethane, dichlorotetrafluoroethane), hydrocarbon propellants or compressed gases such as nitrogen, nitrous oxide, and carbon dioxide. The aerosol may be housed in any suitable type of container, such as tin-plated steel, aluminum, and glass. Many aerosol containers also include valves for emitting the aerosol, actuators and meters.

Other delivery systems can include time-release, delayed release or sustained release delivery systems. Such systems can avoid repeated administrations of the compounds described above, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the compound of the invention is contained in a form within a matrix such as those described in U.S. Pat. Nos. 4,452,775, 4,667,014, 4,748,034 and 5,239,660 and (b) difusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active compounds for at least 30 days, and preferably 60 days. Long-term sustained release implants are well-known to those of ordinary skill in the art and include some of the release systems described above.

The invention also includes kits. The compounds of the invention can be placed in a vial and be incorporated into a kit to be used in the treatment of a disorder associated with calcium channel activity. In certain embodiments, a medicament for the treatment of cardiovascular disease can also be placed in a vial and included in the same kit. In other embodiments other medicaments for treating a subject having a calcium channel blocking disorder can also be placed in a vial and included in the same kit. The kits can include instructions or other printed material on how to administer the compounds. In certain other embodiments the medicaments for treating a subject having a calcium channel blocking disorder can be part of a kit that does not include the compounds of the invention, but includes instructions or other printed material on how to combine the medicament with the compounds of the invention.

Figure 7:
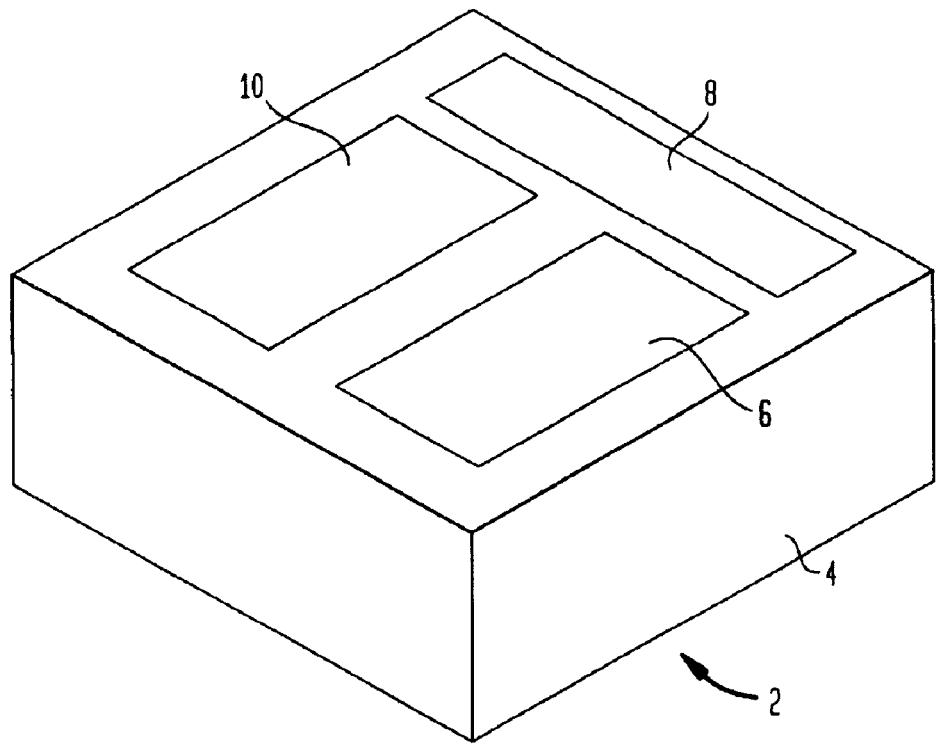
FIG. 7 shows a kit containing the compounds of the invention packaged in a vial and instructions for administering the compounds.

A kit embodying features of the present invention, generally designated by the numeral 2, is illustrated in FIG. 7. Kit 2 is comprised of the following major elements: packaging 4, a dosage form 6, a dosage form 10 and instructions 8. Packaging 4 can be a box-like structure for holding dosage form 6, a dosage form 10 and instructions 8. Individuals skilled in the art can readily modify packaging 4 to suit individual needs.

Dosage form 6 comprises compounds of the invention in an effective amount for for treating a subject having a calcium channel blocking disorder. Dosage form 10 comprises a medicament for treating a subject having a calcium channel blocking disorder, such as a medicament for the treatment of cardiovascular disease.

The invention will be more fully understood by reference to the following examples. These examples, however, are merely intended to illustrate the embodiments of the invention and are not to be construed to limit the scope of the invention.

EXAMPLES

Example 1

Synthesis of the Compounds of the Invention

1. Preparation of Intermediate Compounds Useful in the Synthesis of the Compounds of the Invention:

Melting points were determined using MEL-TENP apparatus and are uncorrected. IR spectra were taken with Perkin-Elmer 1420 Ratio Recording infrared spectrophotometer and Nicolet Impact 410 FT-IR spectrophotometer. H NMR spectra were recorded on a Varian T-60 NMR spectrometer with tetramethylsilane (TMS) as an internal standard; the values of chemical shift(s) are given in parts per million (ppm) and coupling constants (J) in hertz (Hz). Progress of the reaction was monitored by TLC on silica gel plate (Whatman, PE SIL G/UV).

S-(4-Methoxybenzyl)thiosalicylic acid. Thiosalicylic acid 15.419 g(0.1 M) was dissolved in 150 mL of dimethylformamide (DMF) and 41.463 g(0.3M) of $K_2CO_3$, was added to the mixture with stirring. To the above solution, 4-methoxybenzyl chloride 15.661 g(0.1M) was added and the mixture was refluxed for 10 hours. The solution then was cooled to room temperature and 150 mL of water was added and the mixture was acidified with 3M HCl. The precipitated material was collected by gravity filtration and washed with acetone to give 27.364 g(99.7%) of white powder with a melting point of 225–227° C. and the following specifications:

IR(KBr)3200–2500 $cm^{-1}$, 1673 $cm^{-1}$, 1510 $cm^{-1}$, 1234 $cm^{-1}$, 1027 $cm^{-1}$.

NMR($CDCl_3$+DMSO-$d_6$)3.7(s,3H), 4.08(s,2H), 6.7–7.8 (m,8H).

1-(4-Methoxybenzyl) piperazine. A solution of 1.077 (12.5 mM) of piperazine in 20 mL of absolute ethanol was prepared in a 125-mL of Erlenmeyer flask, and was warmed in a bath at 65° C. 1.988 g(12.5 mM) of piperazine dihydrochloride hydrate was dissolved in the solution, by swirling. Under continuous heat at 65° C. 1.958(12.5 mM) of 4-methoxybenzyl chloride was added with vigorous stirring, for five minutes. The separation of white needles commenced almost immediately. After the solution had been stirred for an additional 25 minutes at 65° C., it was cooled, and kept in an ice bath for about 30 minutes. The crystals of piperazine dihydrochloride hydrate were collected by suction filtration, washed with three 5 mL portions of ice-cold absolute ethanol, then dried. Recovery of the dihydrochloride was 1.748 g(88%). Filtrate from this solution was evaporated to dryness at reduced pressure, and crude 1-(4-methoxybenzyl)-4-piperazinium chloride remained as a residue.

In order to remove any piperazine dihydrochloride, the material was heated in about 20 ml of absolute ethanol to produce crystals which were rapidly filtered. Concentration of the filtrate followed by cooling produced 2.629 g(87%) of 1-(4-methoxybenzyl)-4-piperazinium chloride in the form of a white crystal having a melting point of 154–157° C. A solution of this salt in 20 ml of water was made alkaline (pH>12) with about 20 ml of 5N sodium hydroxide solution, extracted with $CH_2Cl_2$ and then dried over $MgSO_4$ for 30 minutes. Filtration, followed by solvent evaporation at reduced pressure, produced a white solid which was crystallized from petroleum ether to give (1.393 g, 54%) of the product having a melting point of 99–101° C. and the following specifications:

IR(KBr) 3392 $cm^{-1}$, 2943 $cm^{-1}$, 1509 $cm^{-1}$, 1301 $cm^{-1}$, 1034 $cm^{-1}$, 991 $cm^{-1}$.

NMR($CDCl_3$)2.12(s,1H), 2.23–2.46(m,4H), 2.53–2.98 (m,4H), 3.40(s,2H), 3.73(s,3H), 6.73–7.29(m,4H).

1-(4-Nitrobenzyl)piperazine hydrochloride. A solution of 1.077 (12.5 mM) of piperazine was prepared in 20 mL of absolute ethanol in a 125-mL of Erlenmeyer flask. The solution was warmed in a bath at 65° C. and 1.988 g(12.5 mM) of piperazine dihydrochloride hydrate was dissolved in the solution, by swirling. Under continuous heat at 65° C., 1.988 g(12.5 mM) of 4-nitrobenzyl chloride was added with vigorous stirring, for five minutes. The separation of white needles commenced almost immediately. The solution was stirred for an additional 25 minutes at 65° C., and kept in an ice bath for about 30 minutes. The crystals of piperazine dihydrochloride hydrate were collected by suction filtration, washed with three 5 mL portions of ice-cold absolute ethanol and then dried. Approximately 4.456 g(224%) of the dihydrochloride was recovered. Filtrate from this solution was evaporated to dryness at reduced pressure and crude 1-(4-Nitrobenzyl)-4-piperazinium chloride was left as a residue.

In order to remove any piperazine dihydrochloride, the material was heated in about 20 mL of absolute ethanol to produce crystals which were rapidly filtered. Concentration of the filtrate followed by cooling produced 0.840 g(26%) of 1-4-Nitrobenzyl)-4-piperazinium chloride in the form of a white crystal having a melting point of 209–212° C.

IR(KBr) 3513 $cm^{-1}$, 2930 $cm^{-1}$, 1514 $cm^{-1}$, 1350 $cm^{-1}$, 1100 $cm^{-1}$, 743 $cm^{-1}$.

NMR(CDCl$_3$) 2.60–2.95(m, 4H), 3.0–3.36(m,$H), 3.60 (s,2H), 7.4–7.2 (m,4H).

1-(4-Fluorobenzyl) piperazine hydrochloride. A solution of 2.154 g(25 mM) of piperazine in 25 mL of absolute ethanol, was warmed in a bath at 65° C. Piperazine dihydrochloride hydrate (3.9765 g(25 mM)) was dissolved in the solution, by swirling. In the bath at 65° C. 3.6145 g(25 mM) of 4-fluorobenzyl chloride was added to the solution with vigorous stirring. The separation of white needles commenced almost immediately. After the solution had been stirred for an additional 25 minutes at 65° C., it was cooled, and the unstirred solution was kept in an ice bath for about 30 minutes. The crystals of piperazine dihydrochloride hydrate were collected by suction filtration, washed with three 5 mL portions of ice-cold absolute ethanol, and then dried. Approximately 3.989 g (100.3%) of the dihydrochloride was recovered. Filtrate from this solution was evaporated to dryness at reduced pressure and crude 1-(4-methoxybenzyl)-4-piperazinium chloride was left as a residue. For removal of any piperazine dihydrochloride, the chloride may be crystallized after rapidly filtering a hot solution in about 20 mL of absolute ethanol. Concentration of the filtrate followed by cooling gave 5.248 g(91%) of 1-(4-fluorobenzyl)-4-piperazinium chloride.

1-(4–Chlorobenzyl) piperazine. A solution of 2.154 g(25 mM) of piperazine in 25 mL of absolute ethanol was warmed in a bath at 65° C. and 3.9765 g(25 mM) of piperazine dihydrochloride hydrate was dissolved in the solution by swirling. Then 4.026 g(25 mM) of 4-chlorobenzyl chloride was added to the solution with vigorous stirring,. The separation of white needles commenced almost immediately. After the solution had been stirred for an additional 25 minutes at 65° C., it was cooled, and the unstirred solution was kept in an ice bath for about 30 minutes. The crystals of piperazine dihydrochloride hydrate were collected by suction filtration, washed with three 5 mL portions of ice-cold absolute ethanol, and then dried. Approximately 4.023 g(101.2%) of the dihydrochloride was recovered. Filtrate from this solution was evaporated to dryness at reduced pressure, crude 1-(4-methoxybenzyl)-4-piperazinium chloride was left as a residue. For removal of any piperazine dihydrochloride, the chloride may be crystallized after rapidly filtering a hot solution in about 20 mL of absolute ethanol. Concentration of the filtrate followed by cooling gave 6.447 g(104%) of 10(4-fluorobenzyl)-4-piperazinium chloride. A solution of this salt was prepared in 15 mL of water and was mixed with about 40 mL of 5 N sodium hydroxide solution. The product was extracted with $CH_2Cl_2$ and dried over $MgSO_4$ for 30 minute. The product was then filtered and the solvent evaporated at reduced pressure to give the 1-(4–Chlorobenzyl) piperazine (2.627 g, 50%). NMR (CDCl$_3$)2.4(s,1H), 2.5–83(m, 4H), 3.0–3.38(m, 4H), 3.45(s, 2H),7.5–7.8(m, 4H).

2. Preparation of S-(4-methoxybenzyl)-N-(2-(N',N'-dimethylamino)ethyl) thiosalicylamide The compound S-(4-methoxybenzyl)-N-(2-(N',N'-dimethylamino)ethyl) thiosalicylamide (compound 1) was prepared by adding 0.02M(823 mg) of the precursor S-(4-methoxybenzyl) thiosalicylic acid to 10 mL of $SOCl_2$, and refluxing for 2 hours followed by removal of the excess $SOCl_2$ under reduced pressure. N,N-dimethyl ethylenediamine (6 mM, 528 mg) was dissolved in 10 mL of ice cold benzene. The acid chloride suspended in benzene was then slowly added to the amine solution. The mixture was stirred overnight at room temperature. Water (20 mL) was added the next day, followed by separation of the aqueous layer. The remaining organic layer was washed with 10% NaOH solution and the aqueous layer was again removed. The aqueous layers were combined and extracted twice with 10 mL of chloroform (CHCl$_3$.) The CHCl$_3$. extracts were combined with the benzene layer and dried over anhydrous MgSO$_4$. Solvents were removed under reduced pressure. The remaining oily product was dissolved in methanol (100 mL), then 600 mL of distilled water were added and the mixture was stirred for 24 hours. The separated crystals were collected with gravity filtration and washed with distilled water, followed by petroleum ether to give 279 mg (27%) of pale yellow crystals having a melting point of 83–84.5° C. and the following specifications:

IR(KBr)3322 $cm^{-1}$, 3257 $cm^{-1}$, 2943 $cm^{-1}$, 1633 $cm^{-1}$, 1511 $cm^{-1}$, 1029 $cm^{-1}$.

NMR(CDCl$_3$)3.2(s,6H), 3.4(t,2H), 3.45(q,4H), 3.7(s,3H), 4.0(s,2H), 6.65–7.59(m8H).

A summary of the elemental analysis of each of compounds 1–5 is presented in Table I below.

3. Preparation of $N^1$-(S-(4-methoxybenzyl) thiosalicyloyl)-$N^4$-methylpiperazine The compound $N^1$-(S-(4-methoxybenzyl) thiosalicyloyl)-$N^4$-methylpiperazine (compound 2) was prepared in a manner similar to that described above for S-(4-methoxybenzyl)-N-(2-(N',N'-dimethylamino)ethyl) thiosalicylamide. After preparing the S-benzylthiosalicyloyl chloride from 0.02M (5.487 g) of S-(4-methoxybenzyl)thiosalicylic acid and 20 mL of $SOCl_2$, the mixture was suspended in warm benzene (30 mL) and was slowly added to a 20 mL cold solution of 4.007 g (0.04M) 1-methylpiperazine in benzene. The mixture was stirred overnight at room temperature. The next day 40 mL of water were added, the aqueous layer was separated, and extracted twice with 15 mL $CH_2Cl_2$. The extracts were combined with the benzene layer, washed with 10% NaOH solution and dried over anhydrous $MgSO_4$. Removal of the solvents under reduced pressure left an oily product which was dissolved in petroleum ether (10 ml). A precipitate separated out upon cooling in an ice bath. The separated solid was collected by suction filtration and washed with petroleum ether to give 3.372 g (47%) of the product in the form of white crystals and having a melting point of 77–78° C. and the following specifications:

IR(KBR) 2943 $cm^{-1}$ 1633 $cm^{-1}$, 1512 $cm^{-1}$, 1440 $cm^{-1}$, 1251 $cm^{-1}$, 1001 $cm^{-1}$.

NMR (CDCl)2.25(s,3H), 2.2–2.5(m,4H), 2.97–3.25(m, 2H), 3.68(s,3H), 3.6–3.85(m,2H), 4.0(s,2H), 6.6–7.25(m, 8H).

4. Preparation of N¹-(S-(4'-methoxybenzyl) thiosalicyloyl)-N piperonylpiperazine N¹-(S-(4'-methoxybenzyl) thiosalicyloyl)-N piperonylpiperazine (compound 3), was prepared by mixing 3 mM(823 mg) of S-(4-methoxybenzyl)thiosalicylic acid and 10 mL of $SOCl_2$ and refluxing the solution for 2 hours. After reflux, the excess $SOCl_2$ was evaporated at reduced pressure. The acid chloride was then suspended in warm benzene (10 mL) and slowly added to an ice cooled solution of 1-piperonylpiperazine (3 mm,661-mg) and triethylamine 94.5 mM, 455 mg) in benzene (10 mL). The mixture was then stirred overnight at room temperature. The next day water (20 mL) was added and the aqueous layer was separated, and extracted twice with 15 mL of $CHCl_3$. The extracts were combined with the benzene layer and was washed with 10% NaOH solution and dried over anhydrous $MgSO_4$. The solvents were removed under reduced pressure to produce an oily product. The product was dissolved in $CHCl_3$ (5ml) and cooled in an ice bath. The product was precipitated with petroleum ether and then was collected by suction filtration and washed with acetone to give 1.144 g (80%) of a white solid having a melting point of 126–127° C. and having the following specifications:

IR(KBr) 1634 $cm^{-1}$, 1517 $cm^{-1}$, 1254 $cm^{-1}$, 1035 $cm^{-1}$.

NMR $CDCl_3$)2.2–2.6(m,4H), 3.0–3.25(m,2H), 3.4(s,2H), 3.78(s,3H), 3.6–3.9(m,2H), 4.0(s,2H), 5.85(s,2M, 6.6–7.3 (ml1H).

5. Preparation of N¹-(S-(4-methoxybenzyl) thiosalicyloyl)-N-(4methoxybenzyl)piperazine The compound N¹-(S-(4-methoxybenzyl) thiosalicyloyl)-N-(4methoxybenzyl)piperazine (compound 4) was prepared as described above using 3 mM(823 mg) of S-(4-methoxybenzyl)thiosalicylic acid, 728 mg (3 mM) of 1-(4-Methoxybenzyl)piperazine, and 1.36 g (13.5 mM) triethylamine. The compound was obtained by dissolving the dark brown oil product in 5 ml of acetone and 20 mL of water then was added to the acetone solution. The separated material was purified by column chromatography on a silica gel column (eluent: Ethyl acetate) to afford 220 mg (16.8%) of the compound having a melting point of 99–101° C. and having the following specifications:

IR(KBr) 2950 $cm^{-1}$, 1635 $cm^{-1}$, 1513 $cm^{-1}$, 1430 $cm^{-1}$, 1251 $cm^{-1}$, 1178 $cm^{-1}$.

NMR($CDCl_3$)2.2–2.6(m,4H), 3.0–3.25(m,2H), 3.4(s,2H), 3.75(s,3H), 3.78(s,3H), 3.6–3.9(m,2H), 4.0(s,2H), 6.6–7.3 (m,12H).

6. Preparation of N¹-(S-(4-methoxybenzyl) thiosalicyloyl)-N-benzylpiperazine

N¹-(S-(4-methoxybenzyl)thiosalicyloyl)-N⁴-benzylpiperazine (compound 5) was prepared using the same procedure described above using: 10 mM(2.743 g) of S-(4-methoxybenzyl) thiosalicylic acid, 3 mM(728 mg) of 1-Benzylpiperazine and 20 mM (3.525 g) triethylamine. The product was dissolved in 5 ml of methylene chloride and purified by column chromatography on a silica gel column (eluent: Ethyl acetate) to give 870 mg (20.1%) of a white crystal. The product was then further purified by crystallization from hexane. The purified product had having a melting point of 84–85° C. and had the following specifications:

IR(KBr) 2817 $cm^{-1}$, 1638 $cm^{-1}$", 1512 $cm^{-1}$, 1250 $cm^{-1}$, 1179 $cm^{-1}$, 1027 $cm^{-1}$.

NMR($CDCl_3$) 2.2–2.6(m,4H), 3.0–3.3(m,2H), 3.5(s,2H), 3.70(s,3H), 3.6–3.96(m,2H), 4.08(s,2H), 6.6–7.3

TABLE 1

|  | C | H | N | S |
|---|---|---|---|---|
| Compound 1 |  |  |  |  |
| Theor. | 66.25 | 7.02 | 8.13 | — |
| Found | 66.09 | 7.14 | 8.14 | — |
| Compound 2 |  |  |  |  |
| Theor. | 67.38 | 6.79 | 7.86 | 9.00 |
| Found | 67.15 | 6.52 | 7.90 | 9.28 |
| Coumpound 3a |  |  |  |  |
| Theor. | 66.78 | 6.01 | 5.77 | 6.60 |
| Found | 66.69 | 6.02 | 5.79 | 6.75 |
| Compound 4 |  |  |  |  |
| Theor. | 70.10 | 6.54 | 6.06 | — |
| Found | 70.34 | 6.80 | 5.83 | — |
| Compound 5 |  |  |  |  |
| Theor. | 72.19 | 6.52 | 6.48 | — |
| Found | 72.11 | 6.69 | 6.46 | — |

7. Preparation of N¹-(S-(4-Methoxybenzyl) thiosalicyloyl)-N-(4-nitrobenzyl)piperazine (compound 6)

N¹-(S-(4-Methoxybenzyl) thiosalicyloyl)-N⁴-(4-nitrobenzyl)piperazine (6) was prepared by refluxing a mixture of 3 mM (823 mg) of S-(4-methoxybenzyl)thiosalicylic acid and 10 mL of $SOCl_2$ for 2 hours, followed by evaporating excess $SOCl_2$ under reduced pressure. The acid chloride was then suspended in warm dioxane (10 mL) and slowly added to an ice cooled mix of 1-(4-nitrobenzyl) piperazine (3 mM, 773 mg) and 10 mL 10% NaOH solution. The mixture was stirred overnight at room temperature. The next day water (70 mL) was added and a white material was precipitated. The product was collected by suction filtration and was washed with acetone to give 602 mg (42%) of a white solid having a melting point 122–123° C. and having the following specifications:

IR(KBr) 2913 $cm^{-1}$, 1622 $cm^{-1}$, 1508 $cm^{-1}$, 1439 $cm^{-1}$, 1179 $cm^{-1}$, 1340 $cm^{-1}$, 1241 $cm^{-1}$, 1024 $cm^{-1}$, 837 $cm^{-1}$.

NMR ($CDCl_3$)2.2–2.6(m,4H), 2.98–3.28(m,2H), 3.55(s, 2H), 3.70(s,3H), 3.6–3.96(m.2H), 4.08(s,2H), 6.6–8.18(m, 12H).

8. Preparation of N1-(S-(4-Methoxybenzyl) thiosalicyloyl)-N-(4-chlorobenzyl)piperazine (compound 7)

N1-(S-(4-Methoxybenzyl)thiosalicyloyl)-N-(4-chlorobenzyl)piperazine (7) was prepared by the same procedure described above for N¹—(S-(4-Methoxybenzyl) thiosalicyloyl)-N-(4-nitrobenzyl)piperazine (6) using 5 mM(1.372 mg) of S-(4-methoxybenzyl)thio) salicyclic acid and 5 mM (1.054 g) of 1-(4-chlorobenzyl)piperazine. The precipitated material was filtered at reduced pressure and washed with methanol. The separated material was purified by column chromatography on a silica gel column (eluent: Ethyl acetate) to produce 496 mg(21%) of the compound having a melting point 109–111.5° C. and having the following specifications:

IR(KBR) 2917 $cm^{-1}$, 1523 $cm^{-1}$, 1581 $cm^{-1}$, 1511 $cm^{-1}$, 1179 $cm^{-1}$, 1427 $cm^{-1}$, 1237 $cm^{-1}$, 1025 $cm^{-1}$, 846 $cm^{-1}$.

NMR (CDCl3)2.0–2.6(m,4H), 2.98–3.28(m,2H), 3.38(s, 2H), 3.68(s,3H), 3.6–3.96(m,2H), 4.0(s,2H), 6.6–7.2(m, 12H).

Preparation of N1-(S-(4-Methoxybenzyl)thiosalicyloyl)-N-(4-fluorobenzyl)piperazine (compound 8)

N1-(S-(4-Methoxybenzyl)thiosalicyloyl)-N-(4-fluorobenzyl)piperazine (8) was prepared by the same procedure described above for $N^1$—(S-(4-Methoxybenzyl) thiosalicyloyl)-N-(4-nitrobenzyl)piperazine (6) and using 5 mM(1.372 mg) of S-(4-methoxybenzyl)thio) salicyclic acid and 5 mM (1.054 g) of 1-(4-fluorobenzyl) piperazine hydrochloride. The product was dissolved in 5 mL of acetone and then 10% NaOH solution (10 mL) and 40 mL of water were added. After overnight incubation the precipitated material was collected by suction filtration to give 872 mg (39%) having a melting point 73–74° C. The product was further purified by recrystallization from chloroform and petroleum ether to give white crystals with a melting point 84–85° C. and having the following specifications:

IR(KBr) 2917 $cm^{-1}$, 1623 $cm^{-1}$, 1581 $cm^{-1}$, 1511 $cm^{-1}$, 1179 $cm^{-1}$, 1427 $cm^{-1}$, 1237 $cm^{-1}$, 1025 $cm^{-1}$, 846 $cm^{-1}$.

NMR (CDCl3)2.0–2.6(m,4H), 2.98–3.28(m,2H), 3.38(s, 2H), 3.68(s,3H), 3.6–3.96(m,2H), 4.0(s,2H), 6.6–7.2(m, 12H).

Example 2

In Vitro Analysis of Test Compounds for Calcium Channel Blocking Activity

To test the compounds of the invention for calcium channel blocking activity, male Wistar rats (Charles River Laboratory, ±200 g) were euthanized with an overdose of sodium pentobarbital (100 mg/kg). The thoracic aorta was removed and cut into 3–4 mm in width and about 30 mm in length. The preparation was mounted under 2.0 g tension in a 10-mL tissue bath containing Krebs-bicarbonate solution aerated with 95% $O_2$ and 5% $CO_2$ at 37° C. This resting tension was used throughout all experiments. The composition of the Krebs-bicarbonate solution was (in mmol) NaCl, 112; KCl, 5; MgSO4, 1.2; $KH_2PO_4$, 1; $NaHCO_3$,25; $CaCl_2$, 1.25 and glucose, 11.5(pH 7.4). At all times, the tissues were immersed in warm Krebs-bicarbonate solution. The solution was made fresh on each day of an experiment. The tissues were suspended in a 10-mL tissue bath with stainless steel loops and polyester threads. These were carefully placed through the tissue rings. The tissues were suspended from Grass force-displacement transducers connected to a Grass polygraph (model 7H, Grass Instrument CO., Quincy, Mass. ) to measure tissue contraction and relaxation. The temperature of the bath was maintained at 37° C. by a Isotemp Constant Temperature Circulator (Fisher Scientific model 801).

Tissues were allowed to equilibrate for 60 minutes and were washed every 15 minutes with fresh Krebs-bicarbonate solution. After the vascular preparations were equilibrated in the normal Krebs-bicarbonate solution, the solution was replaced with the calcium-free, potassium rich Krebs-bicarbonate solution (excluding $CaCl_2$ and with NaCl and KCl concentrations of 17 and 100 mmol, respectively) to cause a depolarization and the $CaCl_2$ was added to obtain the $Ca^{2+}$ response(1.5 mM). When the maximum response was obtained at 1.5 mM of $Ca^{2+}$, the bath was washed (four times) with $Ca^{2+}$ -free Krebs-bicarbonate solution and the preparation was reequilibrated for approximately 15 minutes. A second (control) response was obtained in the same manner.

Each of the test compounds (S-(4-methoxybenzyl)-N-(2-(N',N'-dimethylamino)ethyl) thiosalicylamide (referred to as compound 1); $N^1$—(S-(4-methoxybenzyl) thiosalicyloyl)-$N^4$-methylpiperazine (referred to as compound 2); $N^1$—(S-(4'-methoxybenzyl) thiosalicyloyl)-N piperonylpiperazine (referred to as compound 3); $N^1$—(S-(4-methoxybenzyl) thiosalicyloyl)-N-(4methoxybenzyl)piperazine (referred to as compound 4); and $N^1$—(S-(4-methoxybenzyl) thiosalicyloyl)-$N^4$-benzylpiperazine (referred to as compound 5)) in varying concentrations ($10^{-5}$, $10^{-6}$, $5\times10^{-6}$, and $10^{-7}$ molar) were incubated in the solution for 10 minutes. Each tissue receive only one concentration of compound. The contractile response to 1.5 mmol $Ca^{2+}$ concentration was determined and the data were expressed as percent-induced relaxation of the initial contraction. These values were used for calculation of $IC_{50}$ value according to Van Rossum (Van Rossum, J. M. Arch-Int. Pharmacodyn., v. 143, p. 299–330 (1963)). Diltiazem was used as a control compound throughout the study. The $IC_{50}$ values of these compounds are summarized below in table 2.

TABLE 2

| Compound # | $IC_{50}(mM)^a$ (±SEM) |
|---|---|
| 1 | 15.81 ± 5.05 |
| $2^b$ | 46.4 |
| 3 | 22.62 ± 2.53 |
| 4 | 6.55 ± 1.00 |
| 5 | 7.38 ± 2.26 |
| 6 | 4.66 ± 1.59 |
| 7 | 5.06 ± 1.80 |
| 8 | 4.34 ± 0.59 |
| Diltiazem | 0.258 ± 0.058 |

$^a IC_{50}$ of calcium antagonist potency on $K^+$-depolarized Wistar rat aortic strips (n = 3–5). Percent inhibition of $Ca^{2+}$ contraction at 1.5 mM of $Ca^{2+}$.
$^b IC_{50}$ of calcium antagonist potency on K+-depolarized Wistar rat aortic strips (n = 1).

Example 3

In Vivo Analysis of Test Compounds for Calcium Channel Blocking Activity.

Methods

To further asses the therapeutic value of the compounds of the invention, each of the compounds was evaluated for antihypertensive activity using anesthetized rats. Male cesarian delivered (CD) rats weighing 450–550 gm, were housed in 12"×24" plastic cages in an animal facility with a schedule of 12 hours of light and 12 hours of dark. Animals had ad lithium access to water and food. Animals were anesthetized with urethane (2 gm/kg, ip). The left carotid artery and right jugular vein were cannulated with PE-50 tubing attached to 1 ml syringe prefilled with saline/heparin solution (100 µ/mL). The PE-50 tubing from the carotid artery was then attached to a grass pulse-transducer (Grass polygraph model 7C) to measure arterial blood pressure and heart rate. Each of the compounds was administered via the jugular vein in an appropriate volume followed by 0.1 ml flush with saline/heparin solution. To determine whether each of the compounds of the invention was effective in decreasing the maximal arterial blood pressure (MAP), doses of 10, 30, 60, 100, 130, 180, 270 and 500 mcg/kg of each compound were administered to different animals and a dose response curve was generated. The compounds were diluted in $H_2O$ to give concentrations of 50, 150, 300 and 500 mcg/mL. After blood pressure and heart rate were stabilized for 10 minutes, the compounds were tested individually. The same dosages of the calcium channel blocker diltiazem were also administered to compare to the test compounds. The base line blood pressure of each animal was measured and was determined as the maximal arterial blood pressure (MAP). After administration of each dose from different compounds, the MAP was determined, and the percent of decrease in MAP was calculated and compared to the response obtained from the same dose of diltiazem.

Results

FIGS. 2–6 illustrate the antihypertensive properties of the compounds of the invention. Compounds 1–5 were administered to rats as described above and the resultant change in MAP is presented in FIGS. 2–6 respectively. In each case the compound of the invention caused a significant reduction in MAP as compared to a control and to Diltiazem. Therefore, the compounds of the invention demonstrated considerable antihypertensive activity.

Each of the foregoing patents, patent applications and references is hereby incorporated by reference. While the invention has been described with respect to certain embodiments, it should be appreciated that many modifications and changes may be made by those of ordinary skill in the art without departing from the spirit of the invention. It is intended that such modification, changes and equivalents fall within the scope of the following claims.

We claim:

1. A method for inhibiting calcium channel activity in a cell having a calcium channel comprising:
   contacting the cell having the calcium channel with a compound in an amount effective to inhibit calcium channels,
   wherein the compound has the general structural formula:

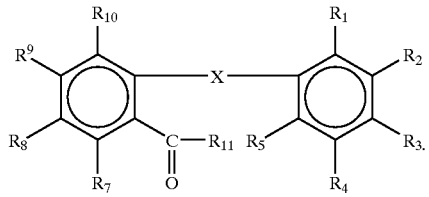

wherein $R_1$, $R_2$, $R_3$, $R_4$, $R_5$, $R_7$, $R_8$, $R_9$, and $R_{10}$ independent of one another, are selected from the group consisting of —H, halogen, piperonyl, ($C_1$–$C_6$) alkyl, ($C_1$–$C_6$) alkenyl, ($C_1$–$C_6$) alkynyl, ($C_1$–$C_6$) alkoxy —CN, —OR', —SR', —NO$_2$, —NR'R', amino acid, —C(O)R', —C(S)R', —C(O)OR', —C(S)OR', —C(O)SR, —C(S)SR', —C(O)N(R')$_2$, —C(O)C(O)R', —C(S)C(O)R', —C(O)C(S)R', —C(S)C(S)R', —C(O)C(O)OR', —C(S)C(O)OR', —C(O)C(S)OR', —C(O)C(O)SR', —C(S)C(S)OR', —C(S)C(O)SR', —C(O)C(S)SR', —C(S)C(S)SR', —C(O)C(O)N(R')$_2$, —C(S)C(O)N(R')$_2$, —C(O)C(S)N(R')$_2$, or —C(S)C(S)N(R')$_2$;

wherein $R_{11}$ is selected from the group consisting of —NH—CH$_2$CH$_2$NH$_2$, —NH—CH$_2$CH$_2$N—(CH$_2$)$_z$—H, —N.(CH$_2$)$_2$N $R_{15}$.(CH$_2$)$_2$, —R', —OR', —SR', —NO$_2$, —N(R')$_2$, —CO—R', —CS—R', —CO—OR', —CS—OR', —CO—SR', —CS—SR', —CO—N(R')$_2$, and —CS—N(R')$_2$;

wherein each R' is (CH$_2$)$_z$—NR"R" and wherein R" is independently selected from the group consisting of ($C_1$–$C_6$) alkyl, ($C_1$–$C_6$) alkenyl, ($C_1$–$C_6$) alkoxy, ($C_1$–$C_6$) alkynyl, ($C_6$–$C_{20}$) aryl, ($C_6$–$C_{20}$) substituted aryl, ($C_6$–$C_{26}$) alkaryl, substituted ($C_6$–$C_{26}$) alkaryl, and ($C_5$–$C_7$) heteroaryl wherein at least one atom of the heteroaryl is selected from the group consisting of a sulfur, a nitrogen, or an oxygen atom, wherein the aryl and alkaryl substituents are each independently selected from the group consisting of hydrogen, halogen, ($C_1$–$C_6$) alkyl, ($C_1$–$C_6$) alkenyl, ($C_1$–$C_6$) alkynyl and trihalomethyl;

wherein z is 1–6;

wherein $R_{15}$ is selected from the group consisting of halogen, ($C_1$–$C_6$) alkyl, ($C_1$–$C_6$) alkenyl, ($C_1$–$C_6$) alkynyl, and ($C_1$–$C_6$) alkoxy;

wherein X is a group having the following formula;

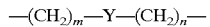

wherein Y is selected from the group consisting of S, N, and O; and wherein m and n, independent of one another, are integers of 0–5.

2. The method of claim 1, wherein $R_{11}$ is selected from the group consisting of —NH—CH$_2$CH$_2$NH$_2$ and —NH—CH$_2$CH$_2$N—(CH$_2$)$_z$—H and wherein Y is S, m is 0 and n is 1–4.

3. The method of claim 2, wherein the compound has the general structural formula:

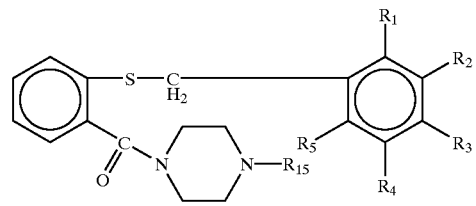

wherein $R_{15}$ is selected from the group consisting of halogen, ($C_1$–$C_6$) alkyl, ($C_1$–$C_6$) alkenyl, ($C_1$–$C_6$) alkynyl, and ($C_1$–$C_6$) alkoxy.

4. A method for inhibiting calcium channel activity in a cell having a calcium channel comprising:
   contacting the cell having the calcium channel with a compound in an amount effective to inhibit calcium channels,
   wherein the compound has the general structural formula:

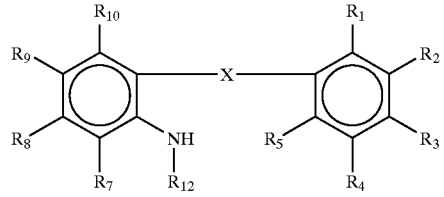

wherein $R_1$, $R_2$, $R_3$, $R_4$, $R_5$, $R_7$, $R_8$, $R_9$, and $R_{10}$ independent of one another, are selected from the group consisting of —H, halogen, piperonyl, ($C_1$–$C_6$) alkyl, ($C_1$–$C_6$) alkenyl, ($C_1$–$C_6$) alkynyl, ($C_1$–$C_6$) alkoxy —CN, —OR', —SR', —NO$_2$, —NR', R', amino acid, —C(O)R', —C(S)R', —C(O)OR', —C(S)OR', —C(O)SR, —C(S)SR', —C(O)N(R')$_2$, —C(O)C(O)R', —C(S)C(O)R', —C(O)C(S)R', —C(S)C(S)R', —C(O)C(O)OR', —C(S)C(O)OR', —C(O)C(S)OR', —C(O)C(O)SR', —C(S)C(S)OR', —C(S)C(O)SR', —C(O)C(S)SR', —C(S)C(S)SR', —C(O)C(O)N(R')$_2$, —C(S)C(O)N(R')$_2$, —C(O)C(S)N(R')$_2$, or —C(S)C(S)N(R')$_2$;

wherein $R_{12}$ is selected from the group consisting of —CO—NH—CH$_2$CH$_2$NH$_2$, —CO—NH—CH$_2$CH$_2$N—(CH$_2$)$_z$—H, and —CO—N.(CH$_2$)$_2$N $R_{15}$.(CH$_2$)$_2$;

wherein each R' is (CH$_2$)$_z$—NR"R" and wherein R" is independently selected from the group consisting of ($C_1$–$C_6$) alkyl, ($C_1$–$C_6$) alkenyl, ($C_1$–$C_6$) alkoxy, ($C_1$–$C_6$) alkynyl, ($C_6$–$C_{20}$) aryl, ($C_6$–$C_{20}$) substituted aryl, ($C_6$–$C_{26}$) alkaryl, substituted ($C_6$–$C_{26}$) alkaryl, and ($C_5$–$C_7$) heteroaryl wherein at least one atom of the heteroaryl is selected from the group consisting of a sulfur, a nitrogen, or an oxygen atom, wherein the aryl and alkaryl substituents are each independently selected from the group consisting of hydrogen, halogen, $(C_1-C_6)$ alkyl, $(C_1-C_6)$ alkenyl, $(C_1-C_6)$ alkynyl and trihalomethyl;

wherein z is 1–6;

wherein $R_{15}$ is selected from the group consisting of halogen, $(C_1-C_6)$ alkyl, $(C_1-C_6)$ alkenyl, $(C_1-C_6)$ alkynyl, and $(C_1-C_6)$ alkoxy;

wherein X is a group having the following formula;

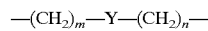
$$-(CH_2)_m-Y-(CH_2)_n-$$

wherein Y is selected from the group consisting of S, N, and O; and wherein m and n, independent of one another, are integers of 0–5.

* * * * *